US006432642B1

(12) United States Patent
Livak et al.

(10) Patent No.: US 6,432,642 B1
(45) Date of Patent: Aug. 13, 2002

(54) BINARY PROBE AND CLAMP COMPOSITION AND METHODS FOR A TARGET HYBRIDIZATION DETECTION

(75) Inventors: Kenneth J. Livak, San Jose, CA (US); Michael Egholm, Wayland, MA (US); Michael W. Hunkapiller, San Carlos, CA (US)

(73) Assignee: PE Corporation (NY), Foster City, CA (US)

( * ) Notice: Subject to any disclaimer, the term of this patent is extended or adjusted under 35 U.S.C. 154(b) by 0 days.

(21) Appl. No.: 09/232,000

(22) Filed: Jan. 15, 1999

(51) Int. Cl.[7] ................ C12Q 1/68; C07H 21/02; C07H 21/04; C12P 19/34; C12N 15/00
(52) U.S. Cl. ............... 435/6; 536/23.1; 536/24.3; 435/91.2; 935/76; 935/77; 935/78
(58) Field of Search ............... 435/6, 91.2; 536/23.1, 536/24.3, 76; 935/77, 78

(56) References Cited

U.S. PATENT DOCUMENTS

| | | | |
|---|---|---|---|
| 4,716,106 A | | 12/1987 | Chiswell |
| 4,868,105 A | | 9/1989 | Urdea et al. |
| 5,424,413 A | * | 6/1995 | Hogan et al. |
| 5,627,032 A | * | 5/1997 | Ulanovsky |
| 5,656,731 A | | 8/1997 | Urdea |
| 5,681,697 A | | 10/1997 | Urdea et al. |
| 5,723,591 A | * | 3/1998 | Livak et al. |
| 5,773,571 A | * | 6/1998 | Nielsen et al. |
| 5,801,155 A | * | 9/1998 | Kutyavin et al. |
| 6,030,787 A | * | 2/2000 | Livak et al. |

FOREIGN PATENT DOCUMENTS

| | | |
|---|---|---|
| EP | 0 204 510 | 12/1986 |
| EP | 0 450 594 | 10/1991 |
| EP | 0 857 791 | 8/1998 |
| GB | 2 202 328 | 9/1988 |

OTHER PUBLICATIONS

Dueholm et al., "Synthesis of Peptide Nucleic Acid Monomers Containing the Four Natural Nucleobases: Thymine, Cytosine, Adenine, and Guanine and Their Oligomerization," *J. Org. Chem.* 59:5767–5773 (1994).

Egholm et al., "Efficient pH–independent sequence–specific DNA binding by pseudoisocytosine–containing bis–PNA," *Nucleic Acids Research*. 23 (2):217–222 (1995).

Gong et al., "New DNA Minor–Groove Binding Molecules with High Sequence–Selectivities and Binding Affinities," *Biochem. and Biophys. Res. Comm.* 240: 557–560 (1997).

Koch et al., "Improvements in automated PNA synthesis using Boc/Z monomers," *J. Peptide Res.* 49: 80–88 (1997).

Lukhtanov et al., "Oligodeoxyribonucleotides with Conjugated Dihydropyrroloindole Oligopeptides: Preparation and Hybridization Properties," *Bioconjugate Chem.* 6: 418–426 (1995).

Mullah et al., "Efficient synthesis of double dye–labeled oligodeoxyribonucleotide probes and their application in a real time PCR assay," *Nuc. Acids Res.* 26(4): 1026–1031 (1998).

van der Laan et al., "A Convenient Automated Solid–Phase Synthesis of PNA–(5')–DNA–(3')–PNA Chimera," *Terrahedron Letters* 38(13): 2249–2252 (1997).

(List continued on next page.)

*Primary Examiner*—Ethan C. Whisenant
(74) *Attorney, Agent, or Firm*—Alex Andrus

(57) ABSTRACT

Binary probe and clamp compositions conduct methods for target hybridization detection. Where the probe is a substrate for exonuclease cleavage, the composition provides quantitation and detection of PCR products, by real-time and end-point measurements. Where the probe is an amplification primer, the composition provides an improved method for labelling and detection of PCR products. Probes and clamps may be labelled with fluorescent dyes, quenchers, hybridization-stabilizing moieties, chemiluminescent dyes, and affinity ligands. Clamps may be nucleic acid analogs, such as 2-aminoethylglycine PNA.

39 Claims, 19 Drawing Sheets fluorescence-quenched hybridized binary probe-clamp composition unhybridized, fluorescent probe     unhybridized clamp

OTHER PUBLICATIONS

Vinayak et al., "Automated Chemical Synthesis of PNA and PNA–DNA Chimera on a Nucleic Acid Synthesizer," *Nucleosides & Nucleotides* 16(7–9): 1653–1656 (1997).

International Search Report dated Jan. 14, 2000 in PCT/US00/00972.

Livak, K.J., et al., "Oligonucleotides with Fluorescent Dyes at Opposite Ends Provide a Quenched Probe System Useful for Detecting PCR Product and Nucleic Acid Hybridization," *Genome Research* 4(6): 357–362 (1995).

Afonina, et al., "Efficient Priming of PCR With Short Oligonucleotides Conjugated to a Minor Groove Binder," *Nucleic Acids Research* 25 (13): 2657–2660 (1997).

Zelphati, O. et al., "PNA–Dependent Gene Chemistry: Stable Coupling of Peptides and Oligonucleotides to Plasmid DNA," *BioTechniques*, 28:304–316 (Feb. 2000).

* cited by examiner

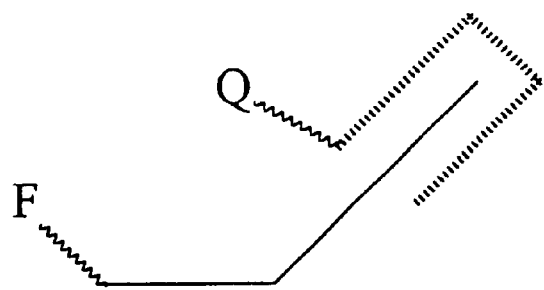
fluorescence-quenched hybridized binary probe-clamp composition
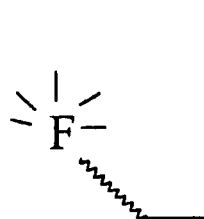
unhybridized, fluorescent probe
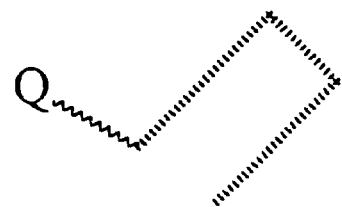
unhybridized clamp
Figure 1

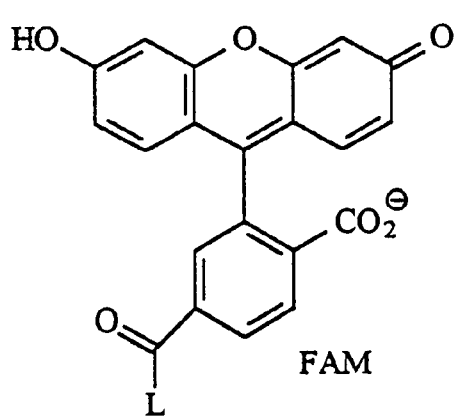
FAM
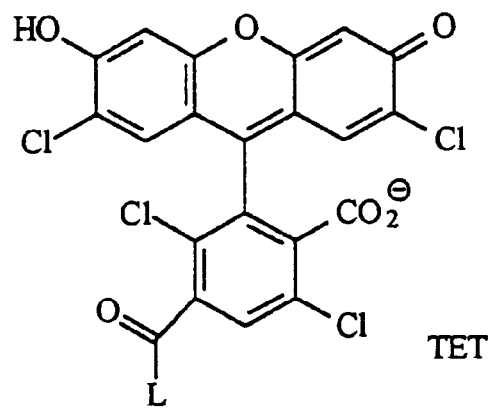
TET
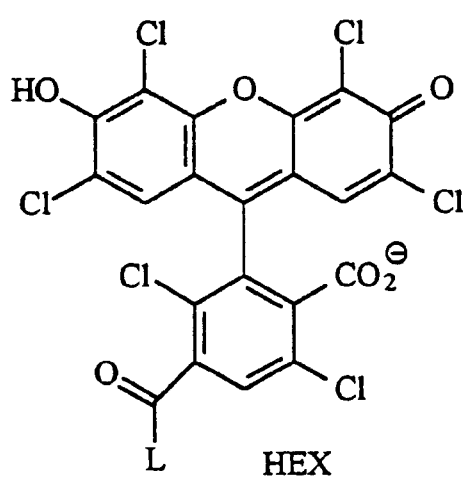
HEX
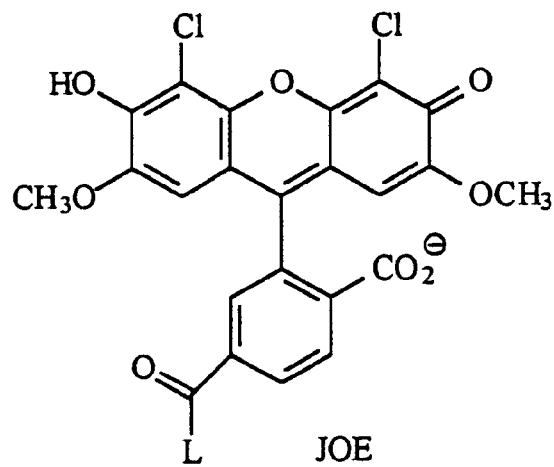
JOE
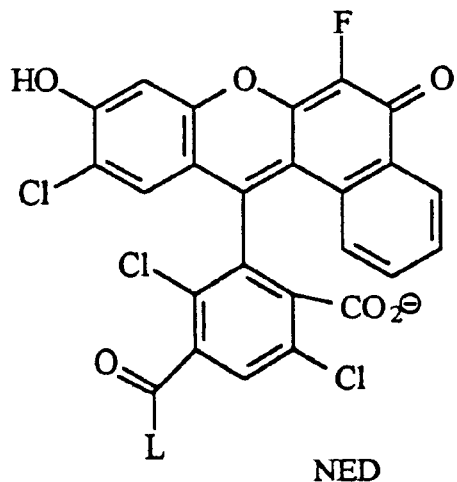
NED
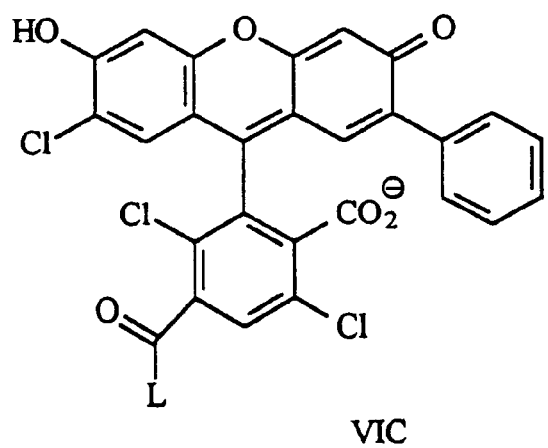
VIC
Figure 9

SEQUENCE LISTING

<160> NUMBER OF SEQ ID NOS: 45

<210> SEQ ID NO 1
<211> LENGTH: 26
<212> TYPE: DNA
<213> ORGANISM: Artificial Sequence
<220> FEATURE:
<223> OTHER INFORMATION: Labelled DNA

<400> SEQUENCE: 1
ctgcccagcc ccagcccaaa ggagga                                   26

<210> SEQ ID NO 2
<211> LENGTH: 28
<212> TYPE: DNA
<213> ORGANISM: Artificial Sequence
<220> FEATURE:
<223> OTHER INFORMATION: Labelled DNA

<400> SEQUENCE: 2
cctgcaggcc cgtgcccgta aaggagga                                 28

<210> SEQ ID NO 3
<211> LENGTH: 31
<212> TYPE: DNA
<213> ORGANISM: Artificial Sequence
<220> FEATURE:
<223> OTHER INFORMATION: Labelled DNA

<400> SEQUENCE: 3
tgctggcacc agacttgccc tcaaaggagg a                             31

<210> SEQ ID NO 4
<211> LENGTH: 31
<212> TYPE: DNA
<213> ORGANISM: Artificial Sequence
<220> FEATURE:
<223> OTHER INFORMATION: Labelled DNA

<400> SEQUENCE: 4
aaaggaggat gctggcacca gacttgccct c                             31

<210> SEQ ID NO 5
<211> LENGTH: 31
<212> TYPE: DNA
<213> ORGANISM: Artificial Sequence
<220> FEATURE:
<223> OTHER INFORMATION: Labelled DNA

<400> SEQUENCE: 5
aaaggaggat gctggcacca gacttgccct c                             31

<210> SEQ ID NO 6
<211> LENGTH: 28
<212> TYPE: DNA
<213> ORGANISM: Artificial Sequence
<220> FEATURE:
<223> OTHER INFORMATION: Labelled DNA

<400> SEQUENCE: 6
aaaggaggac ctgcaggccc gtgcccgt                                 28

<210> SEQ ID NO 7
<211> LENGTH: 31

```
<212> TYPE: DNA
<213> ORGANISM: Artificial Sequence
<220> FEATURE:
<223> OTHER INFORMATION: Labelled 2' OMe RNA/DNA

<400> SEQUENCE: 7
tgctggcacc agacttgccc tcaaaggagg a                              31

<210> SEQ ID NO 8
<211> LENGTH: 31
<212> TYPE: DNA
<213> ORGANISM: Artificial Sequence
<220> FEATURE:
<223> OTHER INFORMATION: Labelled 2' OMe RNA/DNA

<400> SEQUENCE: 8
tgctggcacc agacttgccc tcaaaggagg a                              31

<210> SEQ ID NO 9
<211> LENGTH: 28
<212> TYPE: DNA
<213> ORGANISM: Artificial Sequence
<220> FEATURE:
<223> OTHER INFORMATION: Labelled 2' OMe RNA/DNA

<400> SEQUENCE: 9
cctgcaggcc cgtgcccgta aaggagga                                  28

<210> SEQ ID NO 10
<211> LENGTH: 31
<212> TYPE: DNA
<213> ORGANISM: Artificial Sequence
<220> FEATURE:
<223> OTHER INFORMATION: Labelled DNA analog

<400> SEQUENCE: 10
aaaggaggat gctggcacca gacttgccct c                              31

<210> SEQ ID NO 11
<211> LENGTH: 31
<212> TYPE: DNA
<213> ORGANISM: Artificial Sequence
<220> FEATURE:
<223> OTHER INFORMATION: Labelled DNA analog

<400> SEQUENCE: 11
aaaggaggat gctggcacca gacttgccct c                              31

<210> SEQ ID NO 12
<211> LENGTH: 28
<212> TYPE: DNA
<213> ORGANISM: Artificial Sequence
<220> FEATURE:
<223> OTHER INFORMATION: Labelled DNA analog

<400> SEQUENCE: 12
aaaggaggac ctgcaggccc gtgcccgt                                  28

<210> SEQ ID NO 13
<211> LENGTH: 31
<212> TYPE: DNA
<213> ORGANISM: Artificial Sequence
<220> FEATURE:
<223> OTHER INFORMATION: Labelled DNA analog

<400> SEQUENCE: 13
```
aaaggaggat gctggcacca gacttgccct c                              31

<210> SEQ ID NO 14
<211> LENGTH: 31
<212> TYPE: DNA
<213> ORGANISM: Artificial Sequence
<220> FEATURE:
<223> OTHER INFORMATION: Labelled DNA analog

<400> SEQUENCE: 14
tgctggcacc agacttgccc tcaaaggagg a                              31

<210> SEQ ID NO 15
<211> LENGTH: 28
<212> TYPE: DNA
<213> ORGANISM: Artificial Sequence
<220> FEATURE:
<223> OTHER INFORMATION: Labelled DNA analog

<400> SEQUENCE: 15
cctgcaggcc cgtgcccgta aaggagga                                  28

<210> SEQ ID NO 16
<211> LENGTH: 31
<212> TYPE: DNA
<213> ORGANISM: Artificial Sequence
<220> FEATURE:
<223> OTHER INFORMATION: Labelled DNA analog

<400> SEQUENCE: 16
tgctggcacc agacttgccc tcaaaggagg a                              31

<210> SEQ ID NO 17
<211> LENGTH: 31
<212> TYPE: DNA
<213> ORGANISM: Artificial Sequence
<220> FEATURE:
<223> OTHER INFORMATION: Labelled DNA analog

<400> SEQUENCE: 17
tgctggcacc agacttgccc tcaaaggagg a                              31

<210> SEQ ID NO 18
<211> LENGTH: 28
<212> TYPE: DNA
<213> ORGANISM: Artificial Sequence
<220> FEATURE:
<223> OTHER INFORMATION: Labelled DNA analog

<400> SEQUENCE: 18
aaaggaggac ctgcaggccc gtgcccgt                                  28

<210> SEQ ID NO 19
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (4)..(8)
<223> OTHER INFORMATION: n = pseudo-isocytosine

<400> SEQUENCE: 19
tttnntnntt cctccttt                                             18

<210> SEQ ID NO 20

```
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (4)..(8)
<223> OTHER INFORMATION: n = pseudo-isocytosine

<400> SEQUENCE: 20
tttnntnntt cctccttt                                                   18

<210> SEQ ID NO 21
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (4)..(8)
<223> OTHER INFORMATION: n = pseudo-isocytosine

<400> SEQUENCE: 21
tttnntnntt cctcctt                                                    18

<210> SEQ ID NO 22
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (13)..(17)
<223> OTHER INFORMATION: n = pseudo-isocytosine

<400> SEQUENCE: 22
tcctcctttt ttnntnnt                                                   18

<210> SEQ ID NO 23
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (13)..(17)
<223> OTHER INFORMATION: n = pseudo-isocytosine

<400> SEQUENCE: 23
tcctcctttt ttnntnnt                                                   18

<210> SEQ ID NO 24
<211> LENGTH: 15
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (10)..(14)
<223> OTHER INFORMATION: n = pseudo-isocytosine

<400> SEQUENCE: 24
tcctcctttn ntnnt                                                      15

<210> SEQ ID NO 25
<211> LENGTH: 16
<212> TYPE: DNA
<213> ORGANISM: Artificial Sequence
<220> FEATURE:
```

```
<223> OTHER INFORMATION: Labelled PNA
<221> NAME/KEY: misc_feature
<222> LOCATION: (11)..(15)
<223> OTHER INFORMATION: n = pseudo-isocytosine

<400> SEQUENCE: 25 tcctccttttt nntnnt                                                      16

<210> SEQ ID NO 26
<211> LENGTH: 14
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (9)..(13)
<223> OTHER INFORMATION: n = pseudo-isocytosine

<400> SEQUENCE: 26
tcctccttnn tnnt                                                         14

<210> SEQ ID NO 27
<211> LENGTH: 8
<212> TYPE: DNA
<213> ORGANISM: Artificial Sequence
<220> FEATURE:
<223> OTHER INFORMATION: Labelled PNA

<400> SEQUENCE: 27 tcctcctt                                                                 8

<210> SEQ ID NO 28
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (13)..(17)
<223> OTHER INFORMATION: n = pseudo-isocytosine

<400> SEQUENCE: 28 tcctccttttt ttnntnnt                                                    18

<210> SEQ ID NO 29
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (13)..(17)
<223> OTHER INFORMATION: n = pseudo-isocytosine

<400> SEQUENCE: 29 tcctccttttt ttnntnnt                                                    18

<210> SEQ ID NO 30
<211> LENGTH: 8
<212> TYPE: DNA
<213> ORGANISM: Artificial Sequence
<220> FEATURE:
<223> OTHER INFORMATION: Labelled PNA

<400> SEQUENCE: 30 tcctcctt                                                                 8
```

```
<210> SEQ ID NO 31
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (4)..(8)
<223> OTHER INFORMATION: n = pseudo-isocytosine

<400> SEQUENCE: 31
tttnntnntt cctccttt                                                 18

<210> SEQ ID NO 32
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (4)..(8)
<223> OTHER INFORMATION: n = pseudo-isocytosine

<400> SEQUENCE: 32
tttnntnntt cctccttt                                                 18

<210> SEQ ID NO 33
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (4)..(8)
<223> OTHER INFORMATION: n = pseudo-isocytosine

<400> SEQUENCE: 33
tttnntnntt cctccttt                                                 18

<210> SEQ ID NO 34
<211> LENGTH: 18
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (4)..(8)
<223> OTHER INFORMATION: n = pseudo-isocytosine

<400> SEQUENCE: 34
tttnntnntt cctccttt                                                 18

<210> SEQ ID NO 35
<211> LENGTH: 18
<212> TYPE: DNA
<213> ORGANISM: Artificial Sequence
<220> FEATURE:
<223> OTHER INFORMATION: Labelled 2' OMe RNA
<221> NAME/KEY: misc_feature
<222> LOCATION: (13)..(17)
<223> OTHER INFORMATION: n = pseudo-isocytosine

<400> SEQUENCE: 35 tcctccttt ttnnntnnt                                                 18

<210> SEQ ID NO 36
<211> LENGTH: 18
<212> TYPE: DNA
<213> ORGANISM: Artificial Sequence
```

```
<220> FEATURE:
<223> OTHER INFORMATION: Labelled 2' OMe RNA
<221> NAME/KEY: misc_feature
<222> LOCATION: (13)..(17)
<223> OTHER INFORMATION: n = pseudo-isocytosine

<400> SEQUENCE: 36 tcctccttttt ttnntnnt                                              18

<210> SEQ ID NO 37
<211> LENGTH: 15
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (10)..(14)
<223> OTHER INFORMATION: n = pseudo-isocytosine

<400> SEQUENCE: 37
tcctcctttn ntnnt                                                  15

<210> SEQ ID NO 38
<211> LENGTH: 16
<212> TYPE: DNA
<213> ORGANISM: Artificial Sequence
<220> FEATURE:
<223> OTHER INFORMATION: Labelled 2' OMe RNA
<221> NAME/KEY: misc_feature
<222> LOCATION: (11)..(15)
<223> OTHER INFORMATION: n = pseudo-isocytosine

<400> SEQUENCE: 38 tcctccttttt nntnnt                                                16

<210> SEQ ID NO 39
<211> LENGTH: 14
<212> TYPE: DNA
<213> ORGANISM: Artificial Sequence
<220> FEATURE:
<223> OTHER INFORMATION: Labelled 2' OMe RNA
<221> NAME/KEY: misc_feature
<222> LOCATION: (9)..(13)
<223> OTHER INFORMATION: n = pseudo-isocytosine

<400> SEQUENCE: 39
tcctccttnn tnnt                                                   14

<210> SEQ ID NO 40
<211> LENGTH: 8
<212> TYPE: DNA
<213> ORGANISM: Artificial Sequence
<220> FEATURE:
<223> OTHER INFORMATION: Labelled 2' OMe RNA

<400> SEQUENCE: 40 tcctcctt                                                          8

<210> SEQ ID NO 41
<211> LENGTH: 16
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (11)..(15)
<223> OTHER INFORMATION: n = pseudo-isocytosine, 5-propynyl cytidine

<400> SEQUENCE: 41
```

```
tcctcctttt nntnnt                                                     16
```

<210> SEQ ID NO 42
<211> LENGTH: 14
<212> TYPE: DNA
<213> ORGANISM: Artificial Sequence
<220> FEATURE:
<223> OTHER INFORMATION: Labelled PNA
<221> NAME/KEY: misc_feature
<222> LOCATION: (9)..(13)
<223> OTHER INFORMATION: n = pseudo-isocytosine, 5-propynyl cytidine

<400> SEQUENCE: 42

```
tcctccttnn tnnt                                                       14
```

<210> SEQ ID NO 43
<211> LENGTH: 19
<212> TYPE: DNA
<213> ORGANISM: Artificial Sequence
<220> FEATURE:
<223> OTHER INFORMATION: Labelled DNA

<400> SEQUENCE: 43

```
cctgcaggcc cgtgcccgt                                                  19
```

<210> SEQ ID NO 44
<211> LENGTH: 28
<212> TYPE: DNA
<213> ORGANISM: Unknown
<220> FEATURE:
<223> OTHER INFORMATION: DNA

<400> SEQUENCE: 44

```
gcaaatataa ggtccctgac tactggta                                        28
```

<210> SEQ ID NO 45
<211> LENGTH: 20
<212> TYPE: DNA
<213> ORGANISM: Unknown
<220> FEATURE:
<223> OTHER INFORMATION: DNA

<400> SEQUENCE: 45

```
gtgctgccat gccaggtact                                                 20
```

BINARY PROBE AND CLAMP COMPOSITION AND METHODS FOR A TARGET HYBRIDIZATION DETECTION

FIELD OF THE INVENTION

The invention relates generally to the field of nucleic acid hybridization, and more particularly, to compositions and methods of nucleic acid amplification.

REFERENCES

Agrawal, S. and Zamecnik, P. "Site-specific functionalization of oligonucleotides for attaching two different fluorescent dye groups", Nucleic Acids Research 18:5419–5423 (1990). Andrus, A. "Chemical methods for 5' non-isotopic labelling of PCR probes and primers" (1995) in PCR 2. A Practical Approach, Oxford University Press, Oxford, pp. 39–54.

Barany, F. "The Ligase Chain Reaction in a PCR World", PCR Methods and Applications 1:5–16 (1991).

Beaucage, S. and Iyer, R. "Advances in the synthesis of oligonucleotides by the phosphoramidite approach", Tetrahedron 48:2223–2311 (1992).

Bergot, B., Chakerian, V., Connell, C., Eadie, J., Fung, S., Hershey, N., Lee, L., Menchen, S. and Woo, S. "Spectrally resolvable rhodamine dyes for nucleic acid sequence determination", U.S. Pat. No. 5,366,860, issued Nov. 22, 1994.

Bevan etal, "Sequencing of PCR-amplified DNA", PCR Methods and Applications 1:222–228 (1992).

Blackburn, G. and Gait, M. Eds. "DNA and RNA structure" in Nucleic Acids in Chemistry and Biology, $2^{nd}$ Edition, (1996) Oxford University Press, pp. 15–81.

Boffa, L., Carpaneto, E. and Allfrey, V. "Isolation of active genes containing CAG repeats by DNA strand invasion by a peptide nucleic acid", PNAS (USA) 92:1901–05 (1995).

Bronstein, I. and Voyta, J., "Methods of using chemiluminescent 1,2-dioxetanes" U.S. Pat. No. 4,931,223, issued Jun. 5, 1990.

Bronstein, K., Fortin, J., Stanley, P., Stewart, G. and Kricka, L. "Chemiluminescent and bioluminescent reporter gene assays", Anal. Biochemistry 219:169–81 (1994).

Cardullo, R., Agrawal, S., Flores, C., Zamecnik, P. and Wolf, D. "Detection of nucleic acid hybridization by non-radiative fluorescence resonance energy transfer", Proc. Natl. Acad. Sci. 85:8790–8794 (1988).

Caruthers, M. and Beaucage, S., "Phosphoramidite compounds and processes" U.S. Pat. No. No. 4,415,732, issued Nov. 15, 1983.

Clegg, R. "Fluorescence resonance energy transfer and nucleic acids", Meth. Enzymol. 211:353–388 (1992).

Dueholm, K., Egholm, M., Behrens, C., Christensen, L., Hansen, H., Vulpius, T., Petersen, K., Berg, R., Nielsen, P. and Buchardt, O. "Synthesis of peptide nucleic acid monomers containing the four natural nucleobases: thymine, cytosine, adenine, and guanine and their oligomerization", J. Org. Chem. 59:5767–73 (1994).

Egholm, M., Buchardt, O., Christensen, L., Behrens, C., Freier, S., Driver, D., Berg, R. and Kim, S. "PNA hybridizes to complementary oligonucleotides obeying the Watson-Crick hydrogen bonding rules", Nature 365:566–68 (1993).

Egholm, M., Christensen, L., Dueholm, K., Buchardt, O., Coull, J. and Nielsen, P. "Efficient pH-independent sequence-specific DNA binding by pseudoisocytosine-containing bis-PNA", Nucleic Acids Res. 23:217–22 (1995).

Englisch, U. and Gauss, D. "Chemically modified oligonucleotides as probes and inhibitors", Angew. Chem. Int. Ed. Engl. 30:613–29 (1991).

Froehler, B., Wagner, R., Matteucci, M., Jones, R., Gutierrez, A. and Pudlo, J. "Enhanced triple-helix and double-helix formation with oligodeoxyribonucleotides containing modified pyrimidines" U.S. Pat. No. 5,645,985, issued Jul. 8, 1997.

Froehler, B. and Matteucci, M. "Enhanced triple-helix and double-helix formation with oligomers containing modified purines", U.S. Pat. No. 5,594,121, issued Jan. 14, 1997.

Gelfand, D., Holland, P., Saiki, R., and Watson, R. "Homogeneous assay system using the nuclease activity of a nucleic acid polymerase", U.S. Pat. No. 5,210,015, issued May 9, 1993.

Gong, B. and Yan, Y. "New DNA minor-groove binding molecules with high sequence-selectivities and binding affinities", Biochem. and Biophys. Res. Comm. 240:557–60 (1997).

Hermanson, G. in Bioconjugate Techniques (1996) Academic Press, San Diego, pp. 40–55, 643–671.

Higuchi, R., Fockler, C., Dollinger, G. and Watson, R. "Kinetic PCR: Real time monitoring of DNA amplification reactions", Biotechnology 11:1026–30 (1993).

Higuchi, R., Dollinger, G., Walsh, P., and Griffith, R. "Simultaneous amplification and detection of specific DNA sequences", Biotechnology 10:413–17 (1992).

Holland, P., Abramson, R., Watson, R. and Gelfand, D. "Detection of specific polymerase chain reaction product by utilizing the 5' to 3' exonuclease activity of Thermus aquaticus DNA polymerase", Proc. Natl. Acad. Sci. 88:7276–80 (1991).

Ju, J., Kheterpal, I., Scherer, J., Ruan, C., Fuller, C., Glazer, A. and Mathies, R. "Design and Synthesis of fluorescence energy transfer dye-labeled primers and their application for DNA sequencing and analysis", Analytical Biochemistry 231:131–140 (1995).

Koch, T., Hansen, H., Andersen, P., Larsen, T., Batz, H., Otteson, K. and Ørum, H. "Improvements in automated PNA synthesis using BOC/Z monomers", J. Peptide Res. 49:80–88 (1997).

Kricka, L. in Nonisotopic DNA Probe Techniques (1992), Academic Press, San Diego, pp. 3–25 28.

Kubista, M. and Svanvik, N. "Probe for analysis of nucleic acids", WO 97/45539, Intl. Publ. Date Dec. 4, 1997.

Kutyavin, I., Lukhtanov, E., Gamper, H. and Meyer, R. "Covalently linked oligonucleotide minor groove binder conjugates", WO 96/32496, Intl. Publ. Date Oct. 17, 1996.

Kutyavin, I., Rhinehart, R., Lukhtanov, E., Gorn, V., Meyer, R. and Gamper, H. "Oligonucleotides containing 2-aminoadenine and 2-thiothymine act as selectively binding complementary agents", Biochemistry 35:11170–11176 (1996).

Lawyer, F., Stoffel, S., Saiki, R., Myambo, K., Drummond, R. and Gelfand, D. "Isolation, characterization, and expression in Escherichia coil of the DNA polymerase gene from the extreme thermophile, Thermus aquaticus", J. Biol. Chem. 264:6427–37 (1989).

Livak, K., Flood, S., Marmaro, J., Giusti, W. and Deetz, K. "Oligonucleotides with fluorescent dyes at opposite ends provide a quenched probe system useful for detecting PCR product and nucleic acid hybridization", PCR Methods and Applications 4:357–362 (1995).

Livak, K., Flood, S., Marmaro, J. and Mullah, K. "Self-quenching fluorescence probe", U.S.

Pat. No. 5,723,591, issued Mar. 3, 1998.

Livak, K., Flood, S. and Marmaro, J. "Method for Detecting Nucleic Acid Amplification Using Self-Quenching Fluorescence Probe", U.S. Pat. No. 5,538,848, issued Jul. 23, 1996.

Livak, K., Marmaro, J., and Todd, J. "Towards fully automated genome-wide polymorphism screening", Nature Genetics 9:341–42 (1995).

Lukhtanov, E., Kutyavin, I., Gamper, H. and Meyer, R. "Oligodeoxyribonucleotides with conjugated dihydropyrroloindole oligopeptides: Preparation and hybridization properties", Bioconjugate Chem. 6:418–26 (1995).

Lyman, S., Aster, R., Visentin, G. and Newman, P. "Polymorphism of human platelet membrane glycoprotein IIb associated with Baka/Bakb alloantigen system", Blood 75:2343–2348 (1990).

McPherson, M. J., Quirke, P., and Taylor, G. R. in PCR 2: A Practical Approach (1995) Oxford University Press, Oxford.

Menchen, S., Lee, L., Connell, C., Hershey, N., Chakerian, V., Woo, S. and Fung, S. "4,7-Dichlorofluorescein dyes as molecular probes", U.S. patent 5,188,934, issued Feb. 23, 1993.

Meyer, R. "Incorporation of modified bases in oligonucleotides" in *Protocols for Oligonucleotide Conjugates*, Ed. S. Agrawal (1 994) Humana Press, Totowa, N.J., pp. 73–92.

Mullah, B. and Andrus, A. "Automated synthesis of double dye-labeled oligonucleotides using tetramethylrhodamine (TAMRA) solid supports", Tetrahedron Letters 38: 5751–5754 (1997).

Mullah, B. and Andrus, A. "Solid support reagents for the direct synthesis of 3'-labeled polynucleotides", U.S. Pat. No. 5,736,626, issued Apr. 7, 1998.

Mullah, B., Livak, K., Andrus, A. and Kenney, P. "Efficient synthesis of double dye-labeled oligodeoxyribonucleotide probes and their application in a real time PCR assay", Nucl. Acids Res. 26:1026–1031 (1998).

Nielsen, P. and Christensen, L. "Strand displacement binding of duplex-forming homopurine PNA to a homopyrimidine duplex DNA target", Jour. Amer. Chem. Soc. 118:2287–88 (1996).

Nielsen, P., Egholm, M., Berg, R. and Buchardt, O. "Sequence-selective recognition of DNA by strand displacement with a thymidine-substituted polyamide", Science 254:1497–1500 (1991).

Pemble, S., Schroeder, K., Spencer, S., Meyer, D., Hallier, E., Bolt, H., Ketterer, B. and Taylor, J. B. "Human glutathion S-transferase theta (GSTT1): cDNA cloning and the characterization of a genetic polymorphism" Biochem J. 300:271–276 (1994).

Rumney, S. and Kool, E. "Structural optimization of non-nucleotide loop replacements for duplex and triplex DNAs" J. Amer. Chem. Soc. 117:5636–46 (1995).

Theisen, P., McCollum, C. and Andrus, A. "Fluorescent dye phosphoramidite labelling of oligonucleotides", in *Nucleic Acid Symposium Series* No. 27, Oxford University Press, Oxford, pp. 99–100 (1992).

Van der Laan, A., Brill, R., Kuimelis, R., Kuyl-Yeheskiely, E., van Boom, J., Andrus, A. and Vinayak, R. "A convenient automated solid-phase synthesis of PNA-(5')-DNA-(3')-PNA chimera", Tetrahedron Lett. 38:2249–52 (1997).

Vinayak, R., van der Laan, A., Brill, R., Otteson, K., Andrus, A., Kuyl-Yeheskiely, E. and van Boom, J. "Automated chemical synthesis of PNA-DNA chimera on a nucleic synthesizer", Nucleosides & Nucleotides 16:1653–56 (1997).

Walker, G. et al, "Strand displacement amplification—an isothermal, in vitro DNA amplification technique", Nucleic Acids Research 20: 1691–1696 (1992).

Walker, G., Little, M., Nadeau, J. and Shank, D., "Isothermal in vitro amplification of DNA by a restriction enzyme/DNA polymerase system", Proc. Natl. Acad. Sci. 89:392–96 (1992).

Wittung, P., Nielsen, P. and Norden, B. "Extended DNA-recognition repertoire of peptide nucleic acid (PNA): PNA-dsDNA triplex formation with cytosine-rich homopyrimidine PNA", Biochemistry 36:7973–79 (1997).

Woo, S., Menchen, S. and Fung, S. "Rhodamine phosphoramidite compounds", U.S. Pat. No. 5,231,191, issued Jul. 27, 1993.

Woo, S. and Fung, S. "Solid support reagents for the synthesis of 3'-nitrogen containing polynucleotides", U.S. Pat. No. 5,552,471, issued Sep. 3, 1996.

BACKGROUND

Nucleic acid hybridization assays comprise an important class of techniques in modern biology, with diverse applications in diagnosis of inherited disease, human identification, identification of microorganisms, paternity testing, virology, and DNA sequencing. Primer extension reactions are key components of many nucleic acid hybridization assays and amplification methods. The polymerase chain reaction (PCR) amplification method has enabled advances in cloning, analysis of genetic expression, DNA sequencing, genetic mapping, drug discovery, and the like (Gilliland, 1990; Bevan, 1992; Green, 1991; McPherson, 1995).

The specificity and affinity of two or more strands of nucleic acid and nucleic acid analog molecules hybridizing by Watson/Crick and non-Watson/Crick base pairing are key parameters of efficient nucleic acid hybridization assays. Covalently attached labels, or moieties, which improve or stabilize hybridization are desirable.

Another important aspect of nucleic acid hybridization assays is the method used to facilitate detection of the hybridization event. Fluorescent methods have many advantages over radioisotopes where either the target polynucleotide or the probe or primer can be easily and safely labelled with fluorescent dyes. Methods to lower the costs of labelled probes and primers, or their functional equivalents, are highly desirable. There remains a need for further improvements in the specificity, affinity, and detection of nucleic acid hybridization assays.

SUMMARY

The present invention is directed towards novel binary probe and clamp compositions which are useful in nucleic acid hybridization assays, and methods of using such compositions.

In a first aspect, the invention comprises a binary probe and clamp composition in which the probe comprises a target-specific portion and a clamp-specific portion. The target-specific portion is capable of sequence-specific binding to a target polynucleotide sequence. A clamp comprises a probe-specific portion and a label. The clamp-specific portion of the probe and the probe-specific portion of the clamp form a duplex structure in the binary probe and clamp composition. Alternatively, the clamp-specific portion of the probe and two probe-specific portions of the clamp form a triplex structure.

During a nucleic acid hybridization assay, the target polynucleotide sequence may be detected and quantitated in the sample by detection of the label on the binary composition. The clamp-specific portion of the probe is bound to the probe-specific portion of the clamp during the detection phase of the assay.

The clamp may be an oligonucleotide or a nucleic acid analog. The nucleic acid analog may be comprised of modifications to the internucleotide linkage, the sugar, or nucleobase moieties. A preferred clamp is 2-aminoethylglycine, PNA, (Nielsen, 1991) with the structure

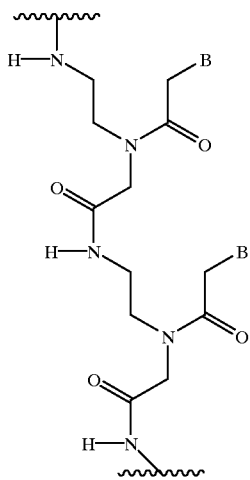

where B is a nucleobase or nucleobase analog.

The probe may be an oligonucleotide or a nucleic acid analog containing nucleobase analogs, sugar analogs, and/or internucleotide analogs.

In a second aspect, the probe or clamp in the binary composition has one or more labels. The probe label can be attached at sites including but not limited to a 5' terminus, a 3' terminus, a nucleobase, an internucleotide linkage, or a sugar. The clamp label can be attached at sites including a terminus, a nucleobase, an internucleotide linkage, a sugar, an amino group, a sulfide group, and a carboxyl group. The labels may include hybridization-stabilizing moieties, fluorescent dyes, fluorescence quenchers, chemiluminescent dyes, amino acids, and affinity ligands.

In a third aspect, a method is provided for detecting a target polynucleotide sequence with the binary probe and clamp composition. In the method, a target-specific portion of the probe hybridizes to a target polynucleotide sequence, and a labelled clamp hybridizes to the probe. The steps of (i) hybridizing the target-specific portion of the probe with the target polynucleotide sequence; (ii) hybridizing the probe-specific portion of the clamp with the clamp-specific portion of the probe; and (iii) detecting the binary probe are conducted to detect a target polynucleotide.

In a fourth aspect, a method is provided for detecting polymerase chain reaction products with a binary probe and clamp composition. In the method, the probe includes a fluorescent dye or quencher, and the clamp includes a fluorescent dye or quencher, such that the binary composition comprises one fluorescent dye and one quencher. The binary composition is largely self-quenching when the probe is hybridized to the clamp. The method is conducted via the steps of (i) hybridizing a target-specific portion of a probe with a target polynucleotide sequence; (ii) hybridizing a probe-specific portion of the clamp with a clamp-specific portion of the probe; (iii) amplifying the target with a DNA polymerase (Lawyer, 1989) with 5' to 3' exonuclease activity, PCR primers, and nucleoside 5' triphosphates, (iv) cleaving the probe by the exonuclease activity of the polymerase, and (v) detecting the fluorescent dye. It is an object of the present invention to detect the labels by monitoring the emitted fluorescence in real-time or at the end-point of target amplification.

In a fifth aspect, a method is provided for labelling polymerase chain reaction products with a binary primer and labelled clamp composition. In the method, a primer has a target-specific portion, capable of sequence-specific binding to a target polynucleotide sequence, and a clamp-specific portion. The clamp includes a label and a primer-specific portion capable of sequence-specific binding to the clamp-specific portion of the primer. The label may be a detectable fluorescent dye. The clamp-specific portion of the primer and the primer-specific portion of the clamp form a duplex structure in the binary primer and clamp composition. Alternatively, the clamp-specific portion of the primer and two primer-specific base-pairing portions of the clamp form a triplex structure in the binary primer and clamp composition. A target polynucleotide is amplified with a DNA polymerase, one or more binary primer and clamp compositions, one or more opposing strand primers, and nucleoside 5' triphosphates, wherein one or more labelled polymerase chain reaction products result.

In a sixth aspect, a method is provided for detecting polymerase chain reaction products where a target polynucleotide is amplified with a primer comprising a target-specific portion at a 3' end and a homopyrimidine sequence portion at a 5' end. A clamp comprising the same homopyrimidine sequence as the 5' end of the target and one or more labels is present in the PCR mixture. The homopyrimidine sequence of the primer is amplified and forms a terminal part of the PCR product. The clamp forms a duplex or triplex structure by hybridization with the PCR product and the label is detected. The label can be a fluorescent dye.

BRIEF DESCRIPTION OF THE DRAWINGS

FIG. 1 Fluorescent dye (F)-probe and quencher (Q)-clamp binary compositions; hybridized and non-hybridized FIG. 2 Hybridization of binary probe and clamp triplex (top) and duplex (bottom) compositions to target polynucleotide FIG. 3 Hybridization of fluorescent dye-labelled probe and quencher clamp composition to target polynucleotide FIG. 4 Hybridization of probe and fluorescent dye-labelled clamp to target polynucleotide FIG. 5 Hybridization of fluorescent dye-labelled probe to quencher/minor groove binder (MGB)-labelled clamp and hybridization of probe to target polynucleotide. Stabilization by MGB of probe binding to target.

During the primer extension reaction, a 5'→3' nuclease activity of the polymerase serves to cut the probe 1 so as to form probe fragments, including fluorescent dye-probe fragment 5 and quencher-labelled clamp with clamp-specific probe fragment 6.

Figure 11:
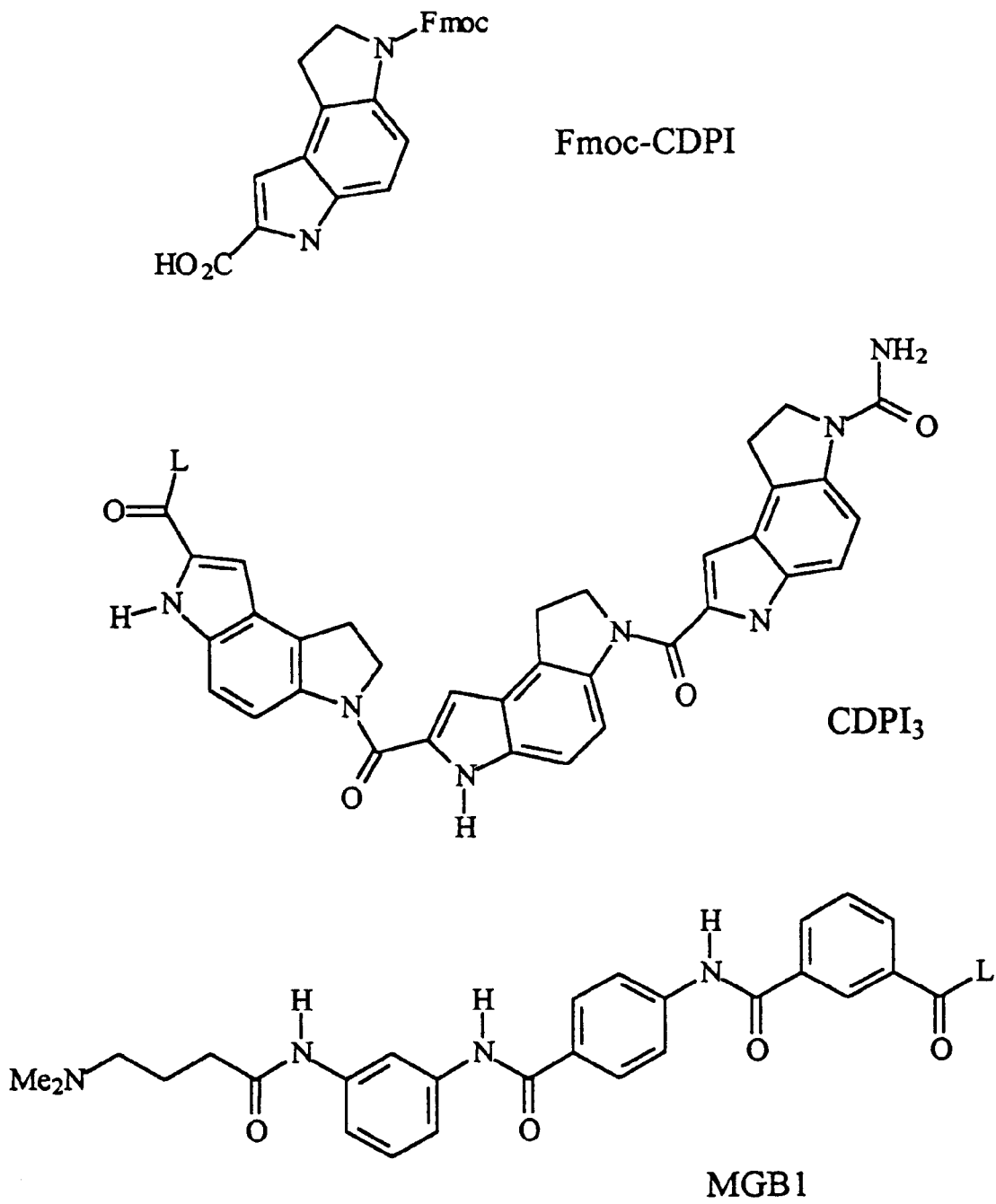
Figure 12:
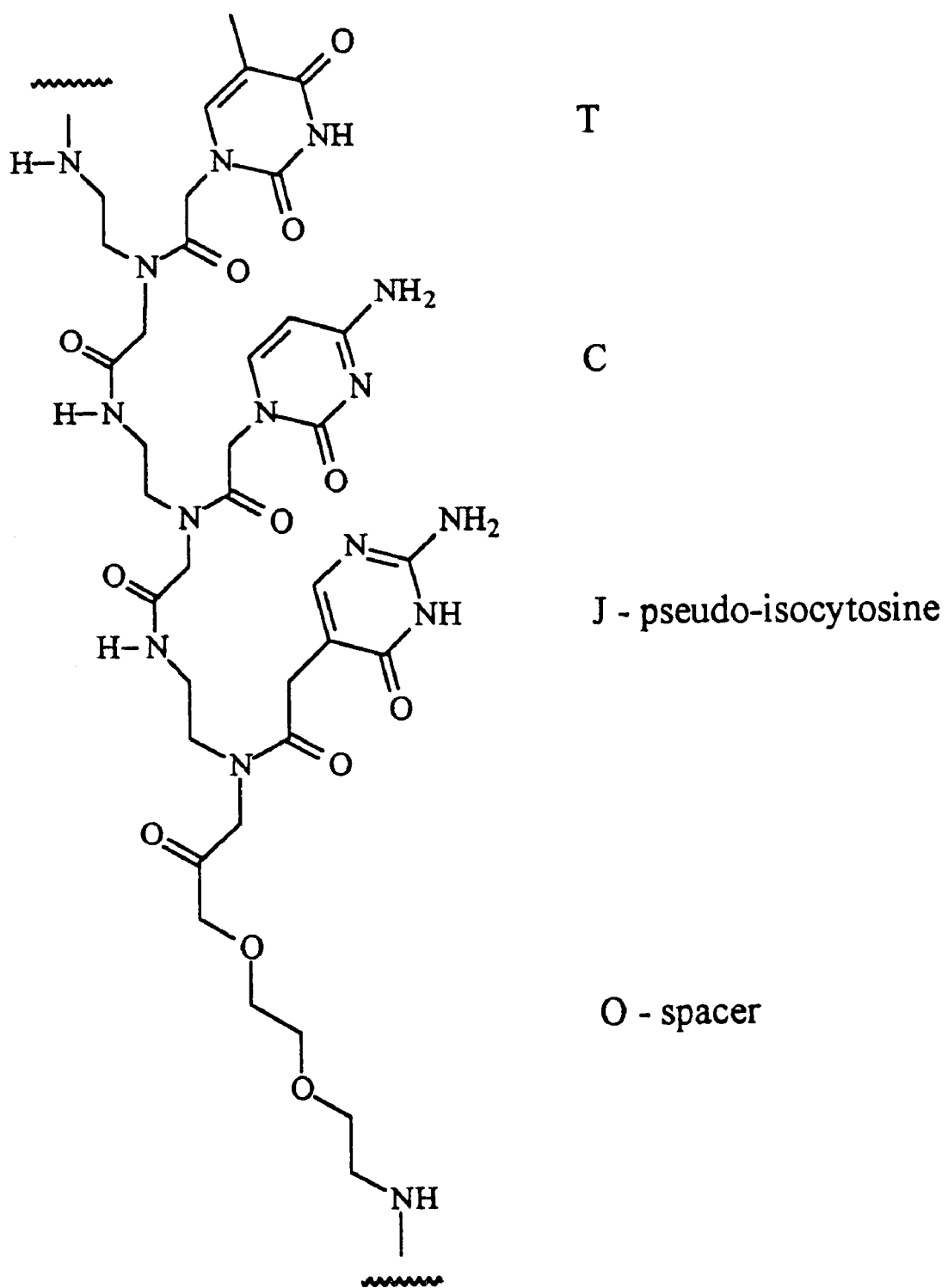

FIG. 9 Fluorescein fluorescent dye structures: FAM, TET, HEX, JOE, VIC, NED, where L is a linker FIG. 10 Quencher structures: TAMRA, ROX, DABCYL, DABSYL, NTB FIG. 11 Minor groove binder structures: MGB1, Fmoc-CDPI, CDPI$_3$ FIG. 12 PNA clamp including monomer units: T, C, pseudo-isocytosine J, and ethyleneoxy spacer O.

Figure 13:
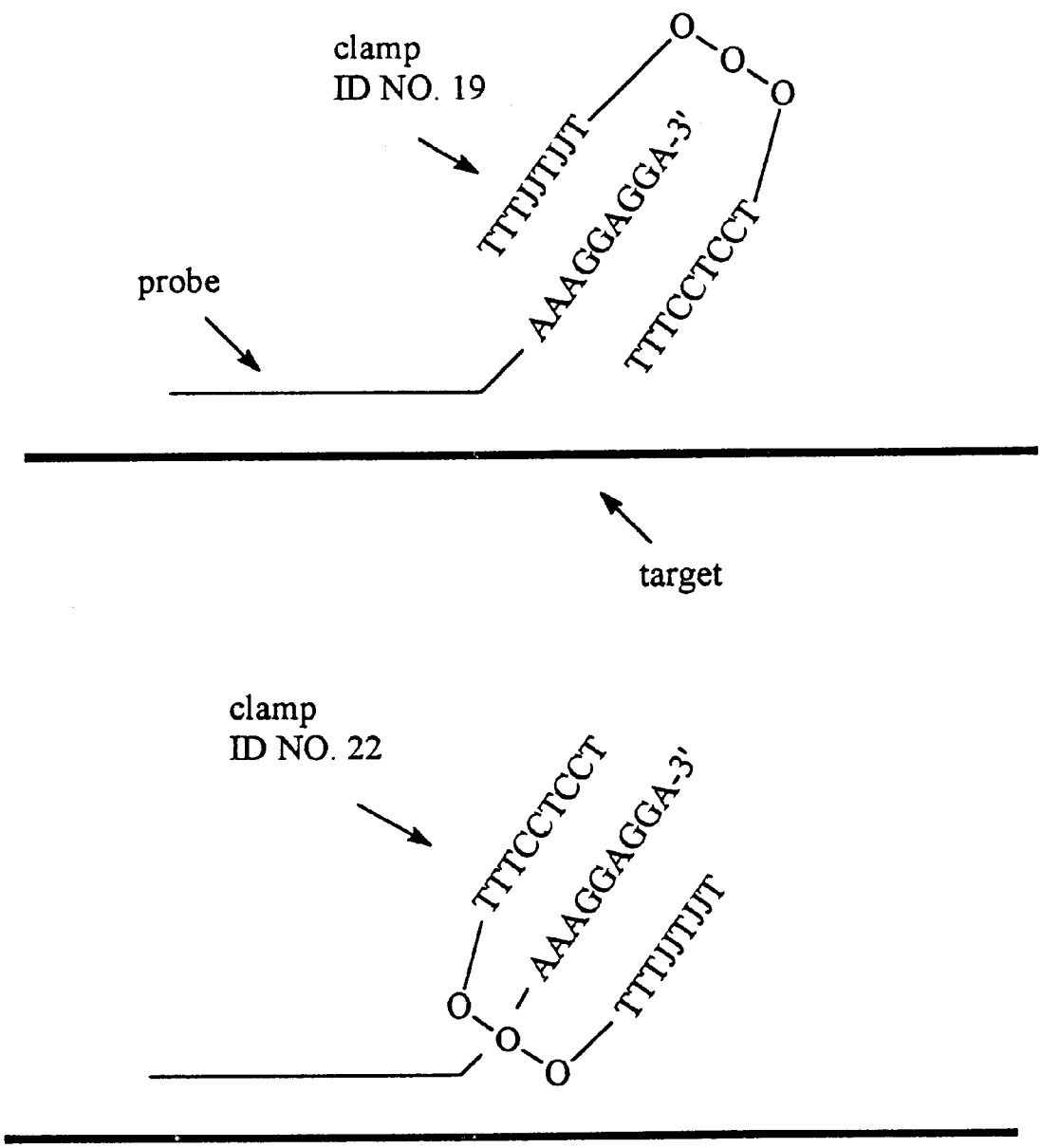

FIG. 13 Binary probe and clamp compositions. Triplex forming clamps, sequences ID NOS. 19, 22 shown without labels.

Figure 14:
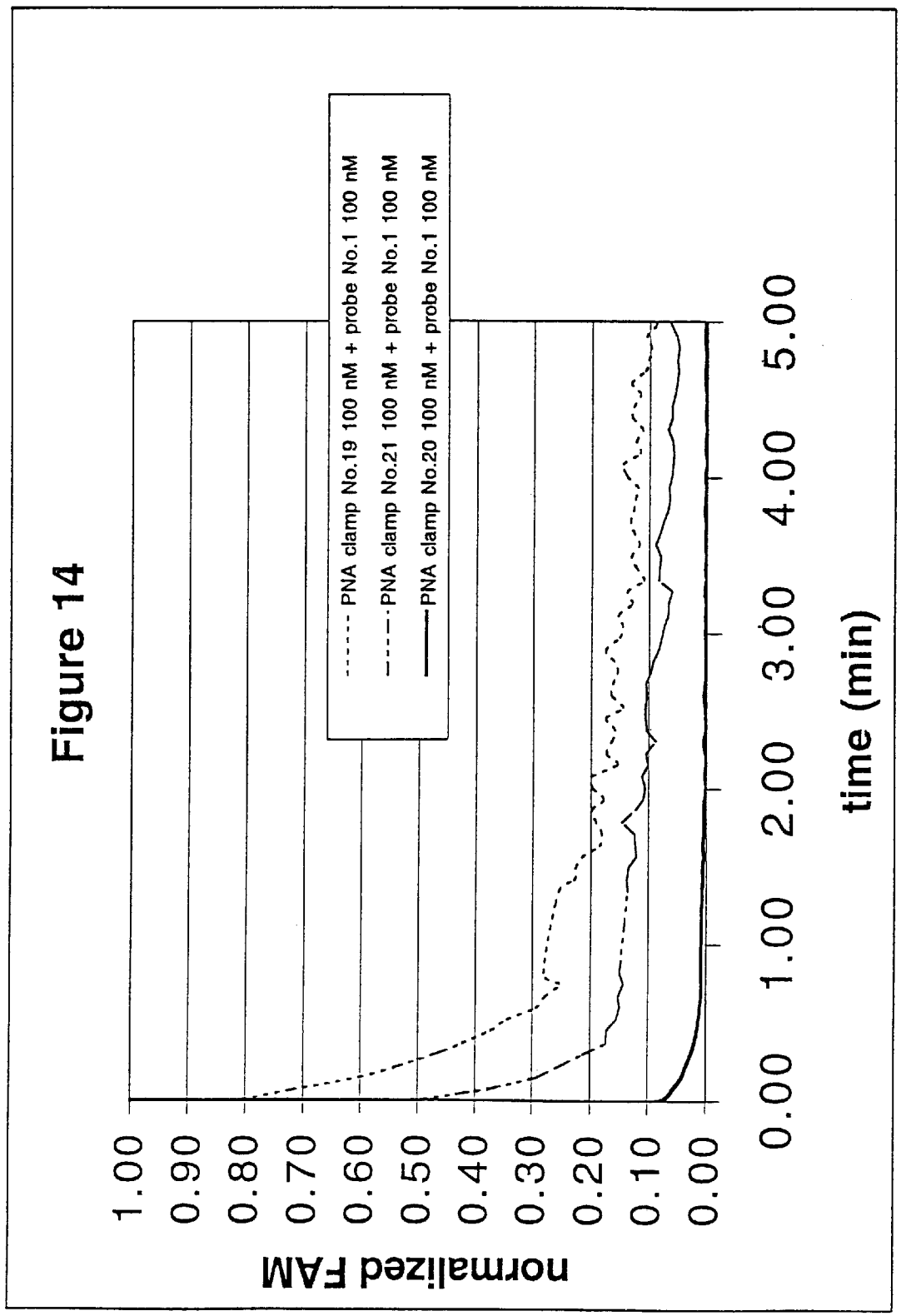

FIG. 14 Rate of hybridization of binary probe and clamp compositions, fluorescence intensity [F] versus time. 100 nM clamp (SEQ. ID NOS. 19, 20, 21), 100 nM probe (SEQ. ID NO. 1), 60° C.; ABI Model 7700.

Figure 15:
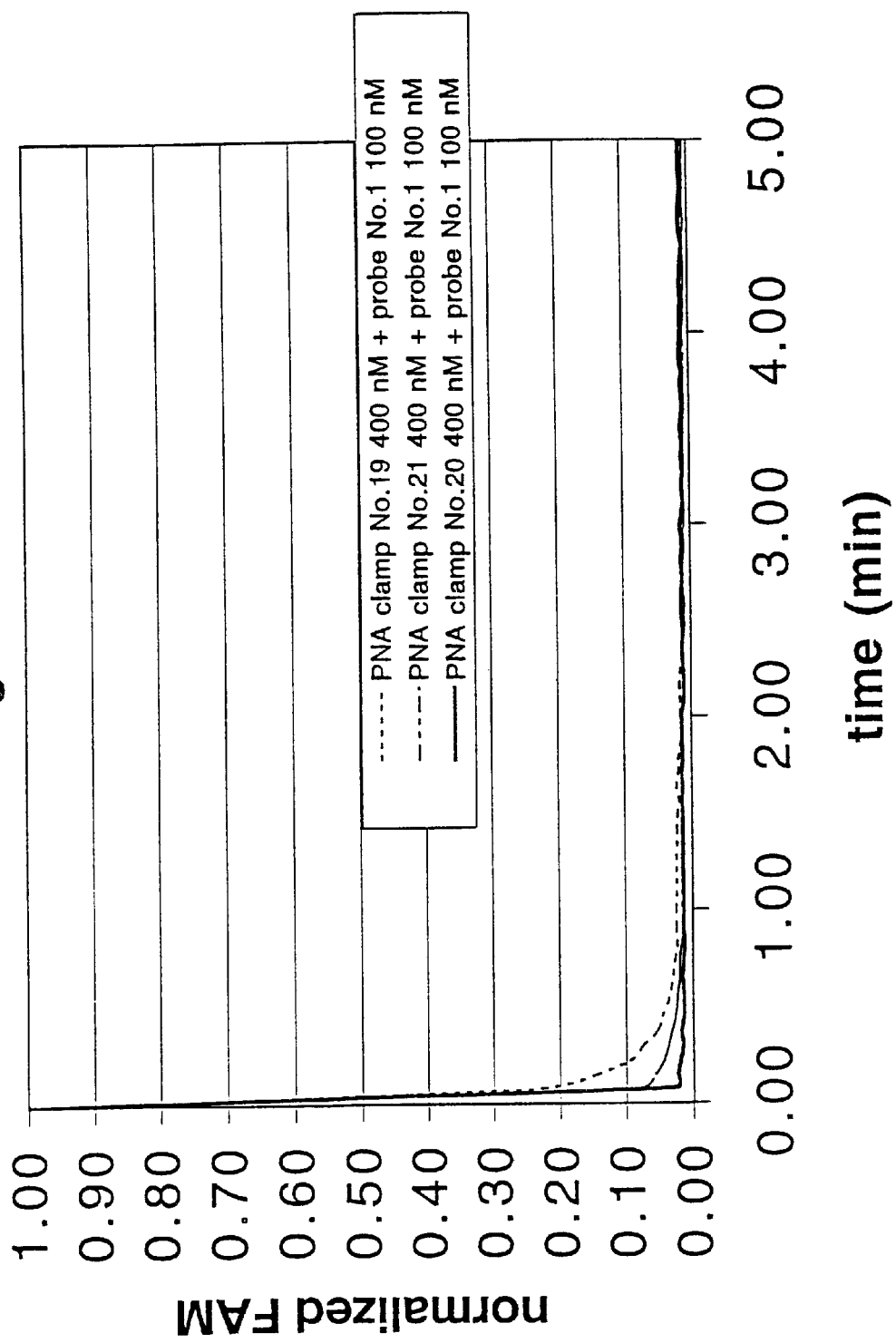

FIG. 15 Rate of hybridization of binary probe and clamp compositions, fluorescence intensity [F] versus time. 100 nM clamp (SEQ. ID NOS. 19, 20, 21), 100 nM probe (SEQ. ID NO. 1), 60° C.; ABI Model 7700.

Figure 16:
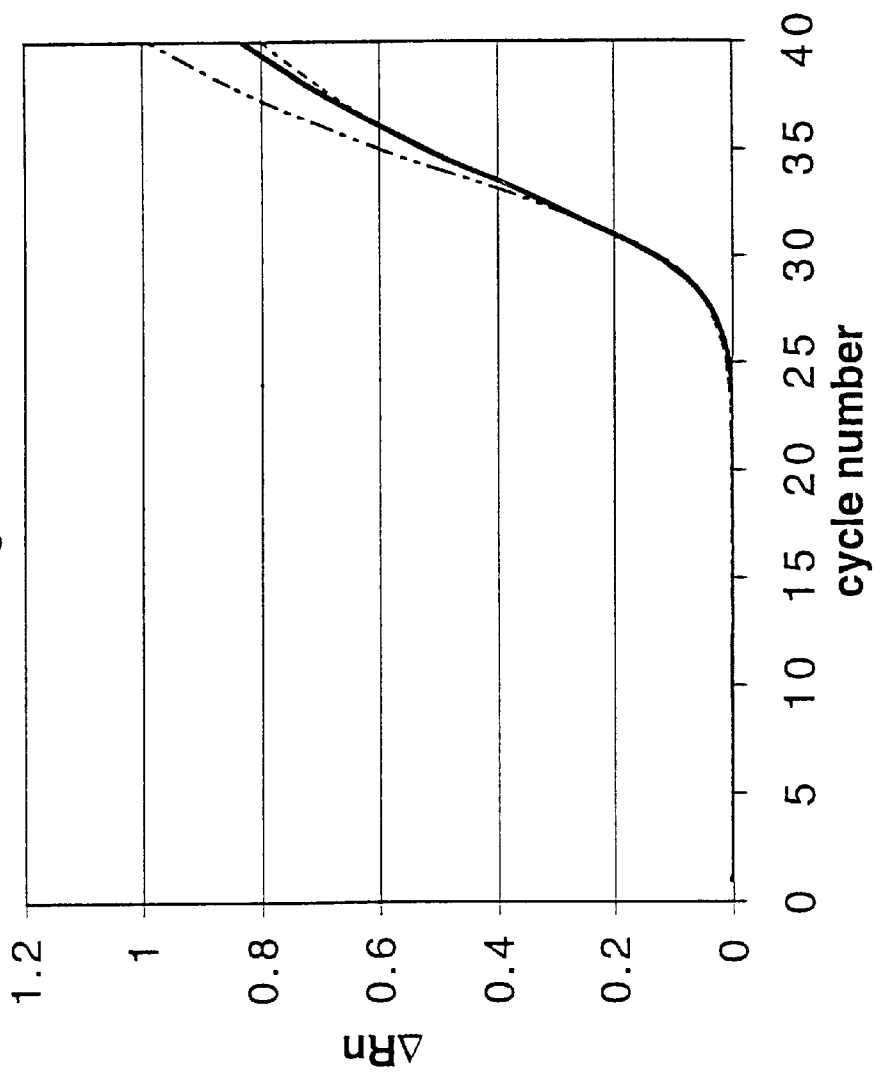

FIG. 16 Real-time PCR detection of BAK target, ΔRn versus cycles, measuring $C_T$, subtracting background fluorescence. Binary probe and clamp compositions: 400 nM clamp (SEQ. ID NO. 19, 20, 21), 100 nM probe (SEQ. ID NO. 1).

Figure 17:
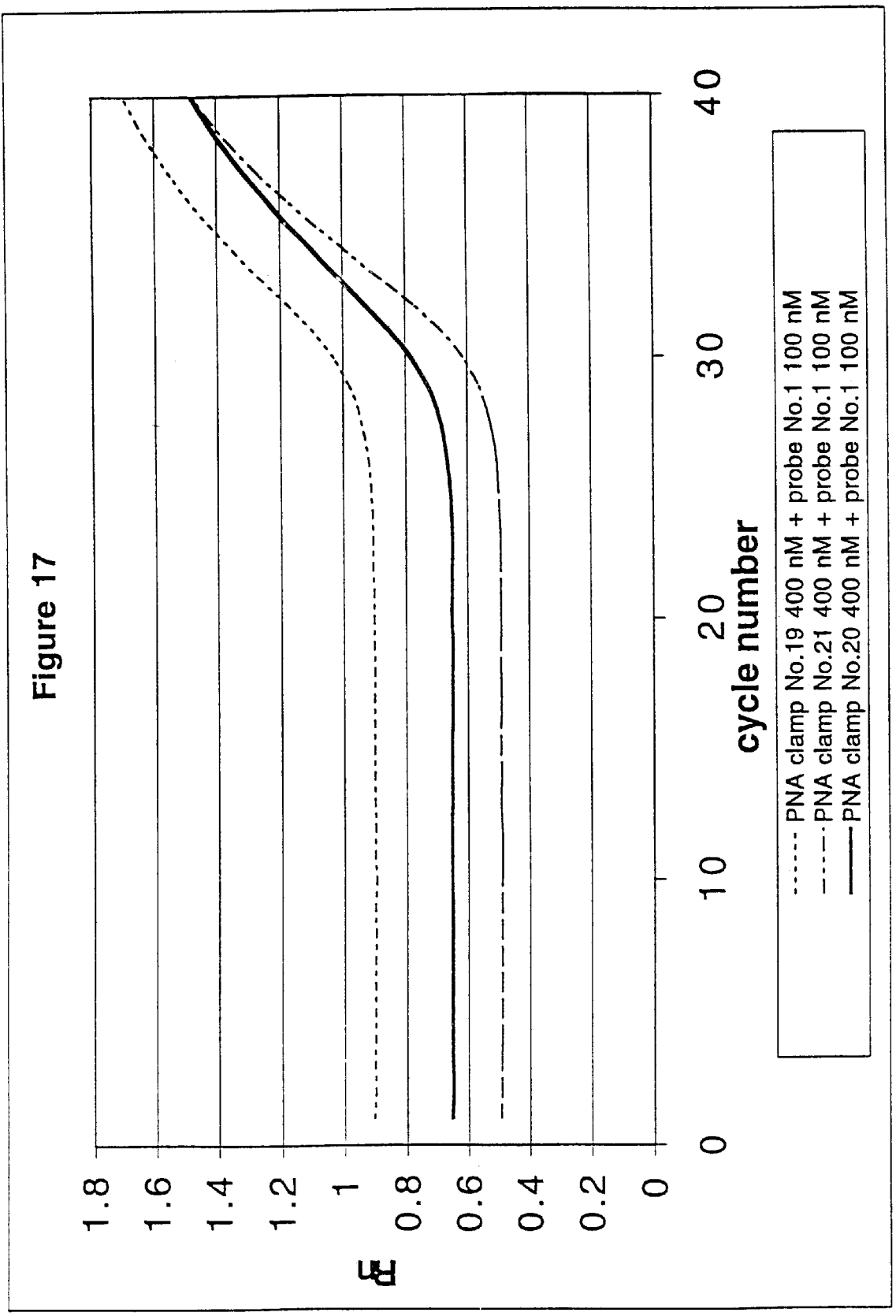

FIG. 17 Real-time PCR detection of BAK target, Rn versus cycles, measuring $C_T$, without subtracting background fluorescence. Binary probe and clamp compositions: 400 nM clamp (SEQ. ID NOS. 19, 20, 21), 100nM probe (SEQ. ID NO. 1).

Figure 18:
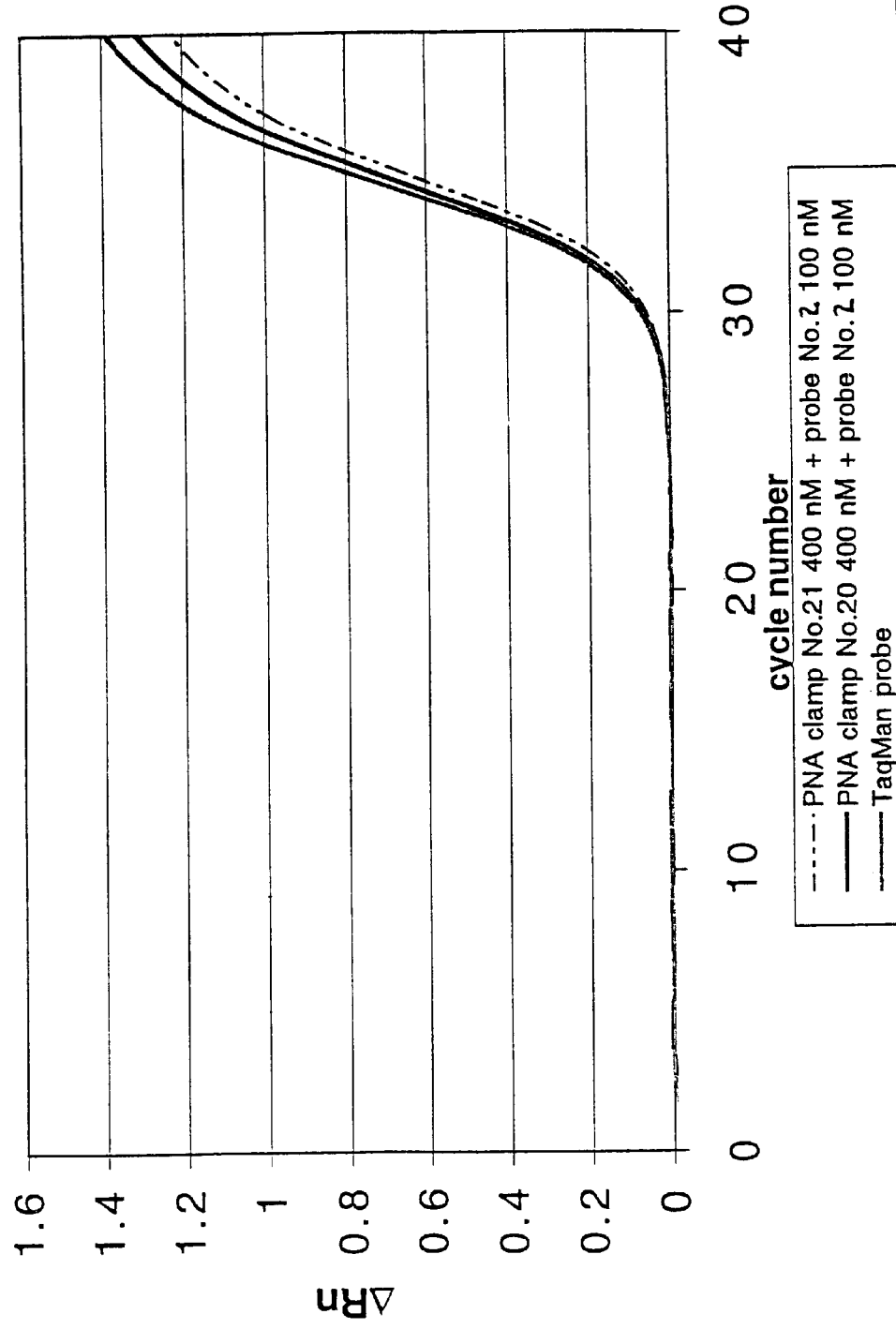

FIG. 18 Real-time PCR detection of GTT1 target, ΔRn versus cycles, measuring $C_T$, subtracting background fluorescence. Binary probe and clamp compositions: 400 nM clamp (SEQ. ID NOS. 20, 21), 100 nM probe (SEQ. ID NO. 2). Taqman probe: 5' FAM-CCTGCAGGCCCGTGCCCGT-TAMRA 3'.

Figure 19:
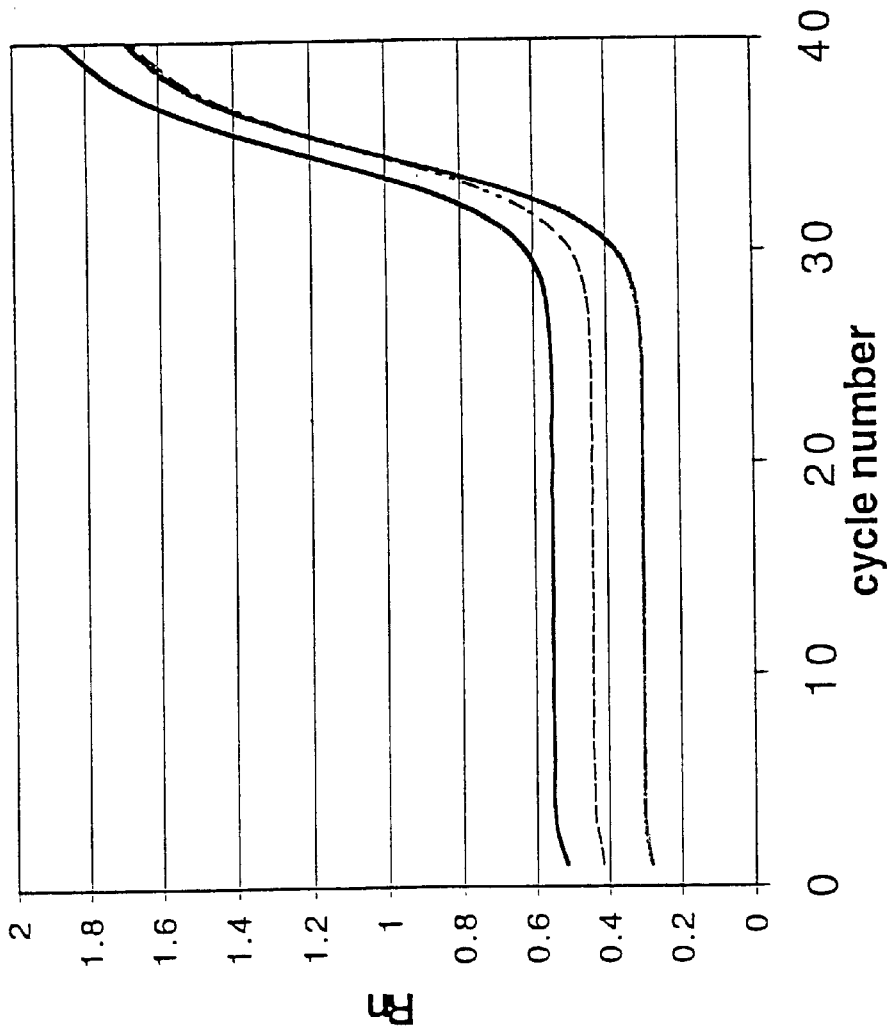

FIG. 19 Real-time PCR detection of GTT1 target, Rn versus cycles, measuring $C_T$, without subtracting background fluorescence. Binary probe and clamp compositions: 400 nM clamp (SEQ. ID NO. 20, 21), 100 nM probe (SEQ. ID NO. 2). Taqman probe: 5' FAM-CCTGCAGGCCCGTGCCCGT-TAMRA 3' (SEQ. ID NO. 43).

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.
Definitions Unless stated otherwise, the following terms and phrases as used herein are intended to have the following meanings:

The terms "nucleic acid", "polynucleotide" or "oligonucleotide" mean polymers of nucleotide monomers or analogs thereof, including double and single stranded deoxyribonucleotides, ribonucleotides, α-anomeric forms thereof, and the like. Usually the monomers are linked by phosphodiester linkages, where the term "phosphodiester linkage" refers to phosphodiester bonds or bonds including phosphate analogs thereof, including associated counterions, e.g., $H^+$, $NH_4^+$, $Na^+$. Polynucleotides typically range in size from a few monomeric units, e.g. 5–40, to several thousands of monomeric units. Whenever a polynucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes deoxythymidine, unless otherwise noted.

"Nucleoside" refers to a compound consisting of a purine, deazapurine, or pyrimidine nucleobase, e.g., adenine, guanine, cytosine, uracil, thymine, deazaadenine, deazaguanosine, and the like, linked to a pentose at the 1'-position. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine.

"Nucleotide" refers to a phosphate ester of a nucleoside, e.g., a triphosphate ester, wherein the most common site of esterification is the hydroxyl group attached to the C-5 position of the pentose. A nucleotide is composed of three moieties: a sugar, a phosphate, and a nucleobase (Blackburn, 1996). When part of a duplex, nucleotides are also referred to as "bases" or "base pairs". The most common naturally-occurring nucleobases, adenine (A), guanine (G), uracil (U), cytosine (C), and thymine (T) bear the hydrogen-bonding functionality that effect Watson/Crick base-pairing.

The term "Watson/Crick base-pairing" refers to a pattern of specific pairs of nucleotides, and analogs thereof, that bind together through sequence-specific hydrogen-bonds, e.g. A pairs with T and U, and G pairs with C.

The term "nucleic acid analogs" refers to analogs of nucleic acids made from monomeric nucleotide analog units, and possessing some of the qualities and properties associated with nucleic acids. Nucleic acid analogs may have modified (i) nucleobase moieties, e.g. C-5-propyne pyrimidine, pseudo-isocytidine and isoguanosine, (ii) sugar moieties, e.g. 2'-O-alkyl ribonucleotides, and/or (iii) internucleotide moieties, e.g. 3'-N-phosphoramidate (Englisch, 1991). A class of analogs where the sugar and internucleotide moieties have been replaced with an 2-aminoethylglycine amide backbone polymer is peptide nucleic acids PNA (Nielsen, 1991).

"Target" refers to a polynucleotide comprising a sequence for hybridization by a primer or probe.

"Attachment site" refers to a site on a probe or clamp to which is attached a linker.

"Linker" refers to one or more atoms comprising a chain connecting a probe or clamp to a label.

"Chimera" as used herein refers to an oligonucleotide including one or more nucleotide and one or more nucleotide analog units.

"Lower alkyl", "lower alkylene" and "lower substituted alkylene" refers to straight-chain, branched, or cyclic groups consisting of 1–12 carbon atoms.

"Label" refers to a moiety covalently attached to an oligonucleotide or nucleic acid analog. One preferred class of labels provides a signal for detection of a molecule by such means as fluorescence, chemiluminescence, and electrochemical luminescence (Kricka, 1992). Another preferred class of labels, hybridization-stabilizing moieties, serve to enhance, stabilize, or influence hybridization of duplexes, e.g. intercalators, minor-groove binders, and cross-linking functional groups. Yet another preferred class of labels serve to effect the separation or immobilization of a molecule by specific or non-specific capture means (Andrus, 1995).

"Detection" refers to detecting, observing, or measuring a molecule on the basis of the properties of a covalently-attached detection label. Detection labels include, but are not limited to, fluorescent dyes, such as fluorescein and rhodamine derivatives, cyanine dyes (Kubista, 1997), and energy-transfer dyes (Clegg, 1992; Cardullo, 1988).

"Probe" refers to an oligonucleotide or nucleic acid analog which may have a target-specific portion and a clamp-specific portion.

"Clamp" refers to an oligonucleotide or nucleic acid analog which has a probe-specific portion. A clamp can bear a label, e.g. a fluorescent dye or quencher, and undergo fluorescence energy transfer when hybridized to a probe bearing a fluorescent dye or quencher moiety. The clamp may also bear other labels, such as minor groove binder or intercalator to stabilize binding of the binary probe composition with a target polynucleotide.

"Primer" refers to a probe capable of selectively annealing to a specified target nucleic acid and thereafter serving as a point of initiation of a primer extension reaction in which the primer is extended in a 5'→3' direction.

The term "primer extension reaction" refers to a reaction between a target/primer duplex and a nucleotide which results in the addition of the nucleotide to a 3'-end of the primer such that the added nucleotide is complementary to the corresponding nucleotide of the target.

The term "5'→3' nuclease activity" refers to an enzyme activity that cleaves nucleic acid at phosphodiester bonds. This activity can be either endo (cleaves at internal phosphodiester bonds) or exo (cleaves at the phosphodiester bond closest to the 5' terminus of the nucleic acid strand.

The term "self-quenching" refers to an intermolecular, energy transfer effect, e.g. a fluorescent dye and quencher are joined on a probe in a configuration that permits energy transfer from the fluorophore to the quencher, resulting in a reduction of the fluorescence by the fluorescent dye.

The term "end-point analysis" refers to a method where data collection occurs only when a reaction is complete. End-point analysis of the exonuclease assay entails fluorescent dye signal measurement when PCR is complete. Results are reported in terms of the change in fluorescence of the fluorescent dye signal from start to finish of the PCR thermal cycling, preferably minus any internal control signals.

The term "real-time analysis" refers to periodic monitoring during PCR. Real-time analysis of the exonuclease assay measures fluorescent dye signal changes from cycle-to-cycle, preferably minus any internal control signals.

II. Design and Synthesis of Binary Compositions

A. Probes and Primers

A probe or primer may be any structure capable of sequence-specific hybridization to a target. Preferably probes and primers are oligonucleotides and nucleic acid analogs. Generally, the design and synthesis of binary compositions of the invention follows conventional teachings. Oligonucleotides and nucleic acid analogs are preferably synthesized on an automated, solid-phase DNA synthesizer using phosphoramidite chemistry (Beaucage, 1992; Caruthers, 1983). The phosphoramidite method of oligonucleotide synthesis is a preferred method because of its efficient and rapid coupling and the stability of the starting nucleoside monomers. Synthesis is typically performed with a growing polynucleotide chain attached to a solid support so that excess reagents in the liquid phase can be easily removed by filtration, thereby eliminating the need for purification steps between cycles.

DNA phosphoramidite nucleoside monomers may be obtained from Perkin-Elmer Co. (Foster City, Calif.) and 2'-OMe RNA monomers may be obtained from Glen Research (Sterling, Va.). The nucleobase protecting groups may be benzoyl ($A^{bz}$ and $C^{bz}$) and dimethylformamidine ($G^{dmf}$) for both the DNA and 2'-OMe RNA nucleosides. The non-nucleosidic PEO linker may be incorporated as a phosphoramidite synthon with the structure below.

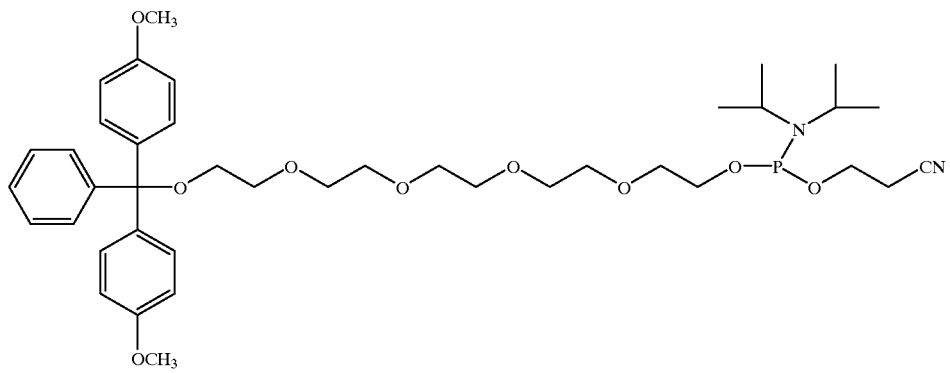

For each coupling cycle of the synthesis at a 0.2 μmole scale, 40 μl of 0.1 M phosphoramidite nucleoside (ca. 3.5 mg) in acetonitrile is delivered concurrently with 120 μl of 0.5 M 5-H tetrazole in acetonitrile. Coupling times are 25 seconds for DNA phosphoramidites and 4 minutes for 2'-OMe RNA phosphoramidites and the PEO phosphoramidite.

After completion of the synthesis, oligonucleotides may be cleaved from the support by treatment with a mixture of $MeQH:t-BuNH_2:H_2O$ (1:1:2) (Woo, 1993) or with concentrated ammonium hydroxide for 1 hr at room temperature as described in the Users Manual for the Applied Biosystems Model 394 DNA/RNA synthesizer. Base protecting groups may be removed by heating the mixture at 85° C. for 1 hr or at 65° C. for 3 h. The oligonucleotides can be analyzed and purified by reverse phase HPLC, anion-exchange HPLC, capillary gel electrophoresis, polyacrylamide gel electrophoresis, and other conventional techniques (Andrus, 1995).

In designing binary probe and clamp compositions, preferably the following general guidelines are followed: (i) the probe is 6–100 nucleotides in length, (ii) if the target nucleic acid sequence is located within a PCR amplicon, the probe sequence should be such that the probe hybridizes at a location on the sequence between the PCR primers; and (iii) the affinity ($T_m$, melting temperature) of the probe/clamp should be the same or higher than the probe/target (Clegg, 1992; Cardullo, 1988; Livak, 1995).

Where the probe includes a label comprising a fluorescent dye and/or quencher, preferably the dye and/or quencher are close enough in the binary probe and clamp composition so that the fluorescence from the fluorescent dye is substantially quenched by the quencher (FIG. 1). The fluorescent dye and/or quencher may be attached at: (i) internal sites on the probe and clamp, (ii) an internal site and the other attached to a terminus of the probe or clamp, or (iii) terminii of the probe and clamp.

B. Clamps

A clamp may be any structure that: (i) conducts sequence-specific hybridization to the clamp-specific portion of a probe of a binary composition and (ii) can bear one or more labels. Preferably, clamps have: (i) high affinity, (ii) high specificity, (iii) high solubility, (iv) non-extendability, (v) chemical stability, and (vi) non-interference with amplification. Preferably, clamps include an oligonucleotides or nucleic acid analog, e.g. PNA. The probe and clamp may form either a duplex or triplex structure (FIG. 2), binding by Watson/Crick and other base-pairing interactions (Froehler, 1997; Rumney, 1995). The clamp has one or more covalently-attached labels. The affinity between the clamp and the probe of the binary composition is strong enough to endure nucleic acid hybridization assay conditions.

In a preferred embodiment, clamps are non-extendable by a polymerase. Examples of non-extendable sugar modifications in the clamp include 3' phosphate, 3' acetyl, 2'-3' dideoxy, and 3' amino, 2'-3' dehydro. The clamp may contain a non base-pairing, non-nucleosidic linker such as ethyleneoxy or polyethyleneoxy. The clamps in the binary composition preferably consist of 6–50 nucleotides and/or nucleotide analogs.

An especially preferred clamp comprises a peptide-nucleic acid oligomer (PNA), a nucleic acid analog in which the natural phosphodiester-deoxyribose backbone has been replaced by N-(2-aminoethyl)-glycine, a peptide-like unit (Nielsen, 1991). PNA clamps of the present invention are capable of base-pairing with complementary sequences in the clamp-specific portion of the probe by Watson/Crick base-pairing. Binding of PNA to a probe can occur in either a parallel or anti-parallel orientation of PNA, although the anti-parallel duplex is much more stable (Egholm, 1993). In the binary composition, where the PNA clamp has been designed to form a triplex structure with two probe- or primer-specific sequences, a hinge region can either be at the 3' terminus of the probe or toward the 5' end of the probe (FIG. 13).

Repeating sequences in the probe-specific portion of the clamp and their complement in the clamp-specific portion of the probe are preferred by virtue of their: (i) high affinity, (ii) high specificity, and (iii) high solubility. A particularly preferred repeating sequence in the probe-specific portion of a duplex-forming clamp is $(CAG)_n$ where the 3 base sequence is repeated from 1 to 10 times (Boffa, 1995; Wittung, 1997). Preferred repeating sequences in the probe-specific portion of a triplex-forming clamp are $(TCC)_n$ and analogs which bind the probe sequence $(GGA)_n$.

PNA clamps can be synthesized using conventional methods on commercially available, automated synthesizers, with commercially available reagents (Dueholm, 1994; Vinayak, 1997; Van der Laan, 1997).

C. Nucleic Acid Analogs in the Binary Probe and Clamp Composition

Probes and clamps may contain various nucleic acid analogs bearing modifications to the nucleobase, sugar, and/or internucleotide moieties.

Preferred nucleobase analog modifications include but are not limited to C-5-alkyl pyrimidines, 2-thiopyrimidine, 2,6-diaminopurine, C-5-propyne pyrimidine, 7-deazapurine, isocytidine, pseudo-isocytidine, isoguanosine, 4(3H)-pyrimidone, hypoxanthine, 8-oxopurines and universal base (Meyer, 1994).

Preferred sugar analog modifications in one or more of the nucleosides include but are not limited to 2'- or 3'-modifications where the 2'- or 3'-position may be hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo.

Other preferred sugar analog modifications include 4'-α-anomeric nucleotides, 1'-α-anomeric nucleotides, 2'-branching group-ribonucleotides, and 2'-O-branching group-ribonucleotides. The structure below illustrates several preferred 2'-sugar modifications.

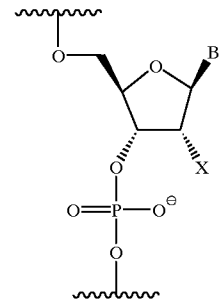

$X = NH_2$, F, Cl, $CH_2CH = CH_2$, and OR where R is $CH_3$, $CH = CHCH_2$, $CH_2CH_2OCH_3$, and lower alkyl

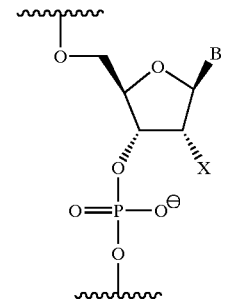

$X = NH_2$, F, Cl, $CH_2CH = CH_2$, and OR where R is $CH_3$, $CH = CHCH_2$, $CH_2CH_2OCH_3$, and lower alkyl Preferred internucleotide analogs between one or more nucleotides include but are not limited to: (i) substitution of oxygen in the internucleotide linkage by sulfur, carbon, or nitrogen, and (ii) sulfate, carboxylate, and amide internucleotide phosphodiester linkages. Other preferred internucleotide analogs include; 2-aminoethylglycine (PNA), 2'-5'-linkage, inverted 3'-3' linkage, inverted 5'-5' linkage, phosphorothioate, phosphorodithioate, methyl phosphonate, non-bridging N-substituted phosphoramidate, alkylated phosphotriester branched structure, and 3'-N-phosphoramidate.

D. Labelling Probes and Clamps

Labels on the probes and clamps of the binary compositions may serve a variety of functions, including facilitation of detection, enhancement of affinity, and stabilization of hybridization. Methods for attachment of labels to oligonucleotides and nucleic acid analogs are well known (Hermanson, 1996). Labels may be attached at various attachment sites including, in the case of oligonucleotides and nucleic acid analogs; (i) the terminii, e.g. 5' and 3' termini of probes, (ii) internucleotide linkages, (iii) sugars, and (iv) nucleobase groups.

Labels, e.g. fluorescent dyes, may be joined to the oligonucleotide or nucleic acid analog by appropriate functionalization of the labels and/or the monomers, e.g. phosphoramidite nucleosides. Detailed description of how to join labels to nucleic acids and analogs can be found liberally in the literature (Theisen, 1992; Andrus, 1995; Hermanson, 1996; Ju, 1995). One method to covalently attach a fluorescent dye and/or a quencher to the 5' hydroxyl of an oligonucleotide is by coupling fluorescent dye and quencher phosphoramidite monomers (Theisen, 1992). These monomers are installed in an acetonitrile solution on the automated synthesizer and coupled as the last monomer to the support-bound oligonucleotide. Alternatively, nucleobase moieties of oligonucleotides can be internally labelled after cleavage from the support and deprotection. A third method is where a nucleophilic reactive group, such as amino or thiol, on the nucleobase can couple with an active ester or other reactive group on a label. As an example, an amino linker attached to the 5-position of cytidine or thymine can couple with an NHS-ester of carboxy-FAM dye to form an amide bond in labelling an oligonucleotide at any predetermined nucleotide within an oligonucleotide (Ruth, 1990; Meyer, 1994). The 5' terminus of oligonucleotides can also be labelled in this manner (Andrus, 1995). Phosphates and phosphate analogs can also be labelled by similar methods (Agrawal, 1990). Solid-phase synthesis supports may bear labels, e.g. fluorescent dyes, to give 3' labelled oligonucleotides (Woo, 1996; Mullah, 1997; Mullah, 1998). The 3' terminal nucleotide of the probe may be further blocked and rendered incapable of extension by a nucleic acid polymerase. Such 3' blocking is conveniently carried out by chemical attachment of a phosphate group (Horn, 1986; commercially available as PhosphaLink, PE Biosystems).

PNA clamps can be labelled at the carboxyl and amino terminii and at the nucleobases by the same activated-ester methods (NHS-) described above for oligonucleotides, and by other conventional methods.

Hybridization-stabilizing moieties include but are not limited to minor groove binders, intercalators, polycations, such as poly-lysine and spermine, and cross-linking functional groups. Hybridization-stabilizing moieties may increase the stability of base-pairing or the rate of hybridization, i.e. affinity. Hybridization-stabilizing moieties serve to increase the specificity of base-pairing, exemplified by large differences in thermal melting temperatures, $T_m$, between perfectly complementary probe and target sequence and where the probe contains one or more mismatches of Watson/Crick base-pairing. Preferred minor groove binders include Hoechst 33258, $CDPI_{1-3}$, MGB1, netropsin, and distamycin (Blackburn, 1996). An example of a minor groove binder is $CDPI_3$ (Kutyavin, 1996; Lukhtanov, 1995) having the structure

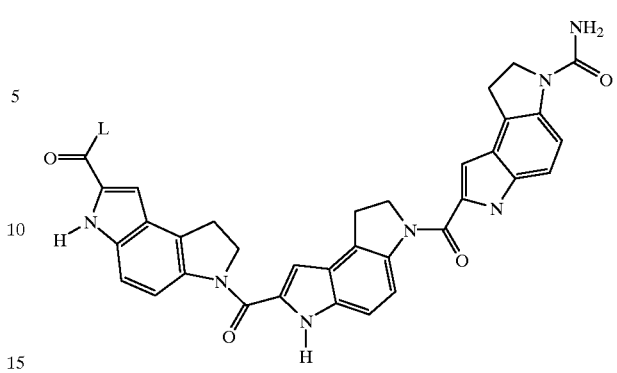

where L is a linker or attachment site for labeling of probes and clamps.

Figure 6:
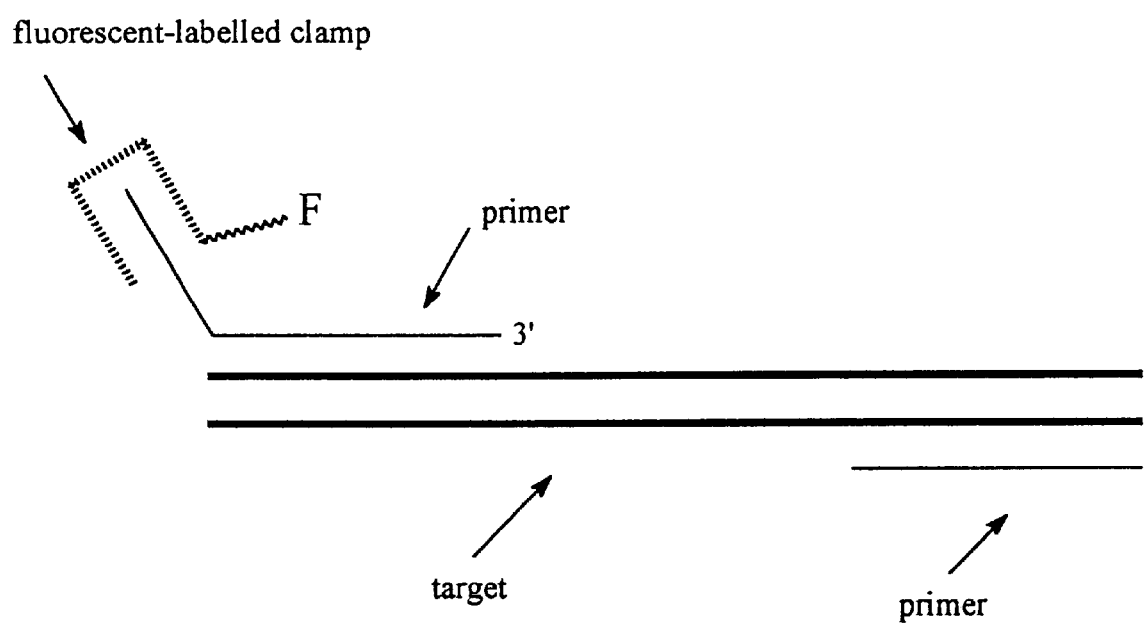
FIG. 6 Hybridization of unlabelled-primer and fluorescent dye-labelled clamp to PCR target FIG. 7 Amplification of target polynucleotide with 5'-homopyrimidine sequence and triplex-forming, fluorescent-labelled clamp binding to 3' homopurine sequence of PCR product FIG. 8 Exonuclease assay whereby triple helix-forming, self-quenching binary probe and clamp composition 1 including a fluorescent dye and a quencher, and target primers 2a and 2b are hybridized to target polynucleotide 3. During the polymerization phase of amplification, the primers 2a and 2b are extended using a polymerase enzyme thereby forming extended primers 4a and 4b.

The carboxyl group of minor groove binders, such as $CDPI_{1-3}$ and MGB1 (FIG. 11) may be activated as NHS esters for coupling to amine groups or as phosphoramidites for direct labelling by automated synthesis. Minor groove binders when labelled to probes or clamps in binary probe and clamp compositions may increase the affinity and specificity of hybridization to some or substantially most target sequences (Blackburn, 1996, p.337–46) (FIG. 6).

Fluorescent dye useful for labelling probes and clamps include; FAM, TET, HEX, JOE, TAMRA, ROX, VIC, NED, dichloro-fluorescein, dichloro-rhodamine, and cyanines (Bergot, 1994, Menchen, 1993). Quenchers include; TAMRA, ROX, DABCYL, DABSYL, malachite green, and cyanines. Cyanines may have the structure

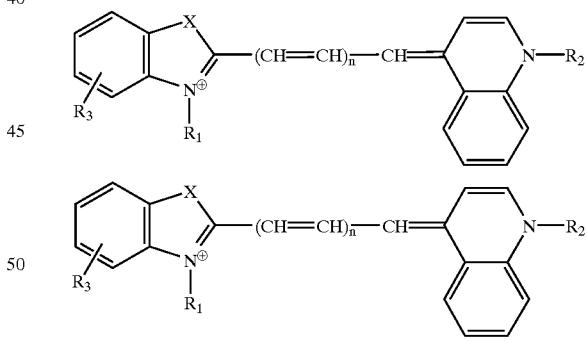

where $R_1$ or $R_2$ is H, lower alkyl, lower alkylene, lower substituted alkylene, phenyl, or aryl; X is S, O, NH, or N—R; $R_3$ is nitro, halo, sulfonate, hydroxy, amino, lower alkyl, or trihalomethyl, and n=0–2 (Kubista, 1997). The attachment site for labelling of probes or clamps may be at $R_1$, $R_2$, or $R_3$.

Another preferred class of labels comprise chemiluminescent compounds. Particularly preferred are chemiluminescent dyes having the structure

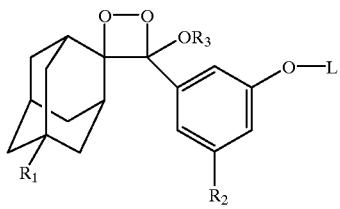

where $R_1$ is hydrogen or halogen; $R_2$ is phosphate, galactoside, glucoside, glucuronide, trialkylsilyloxy, acyloxy, or hydrogen; $R_3$ is methyl, ethyl, and lower alkyl, and L is a linker to the binary composition (Bronstein, 1994; Bronstein, 1990). Affinity ligands include biotin, dinitrophenyl, digoxigenin, cholesterol, polyethyleneoxy, and peptides.

Fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED) and 2'-chloro-7'-phenyl-1,4-dichloro-6-carboxyfluorescein (VIC) (FIG. 9). The 5-carboxy isomers are also useful. Other embodiments of fluorescent dye moieties are cyanine dyes, dansyl derivatives, and the like.

Figure 10:
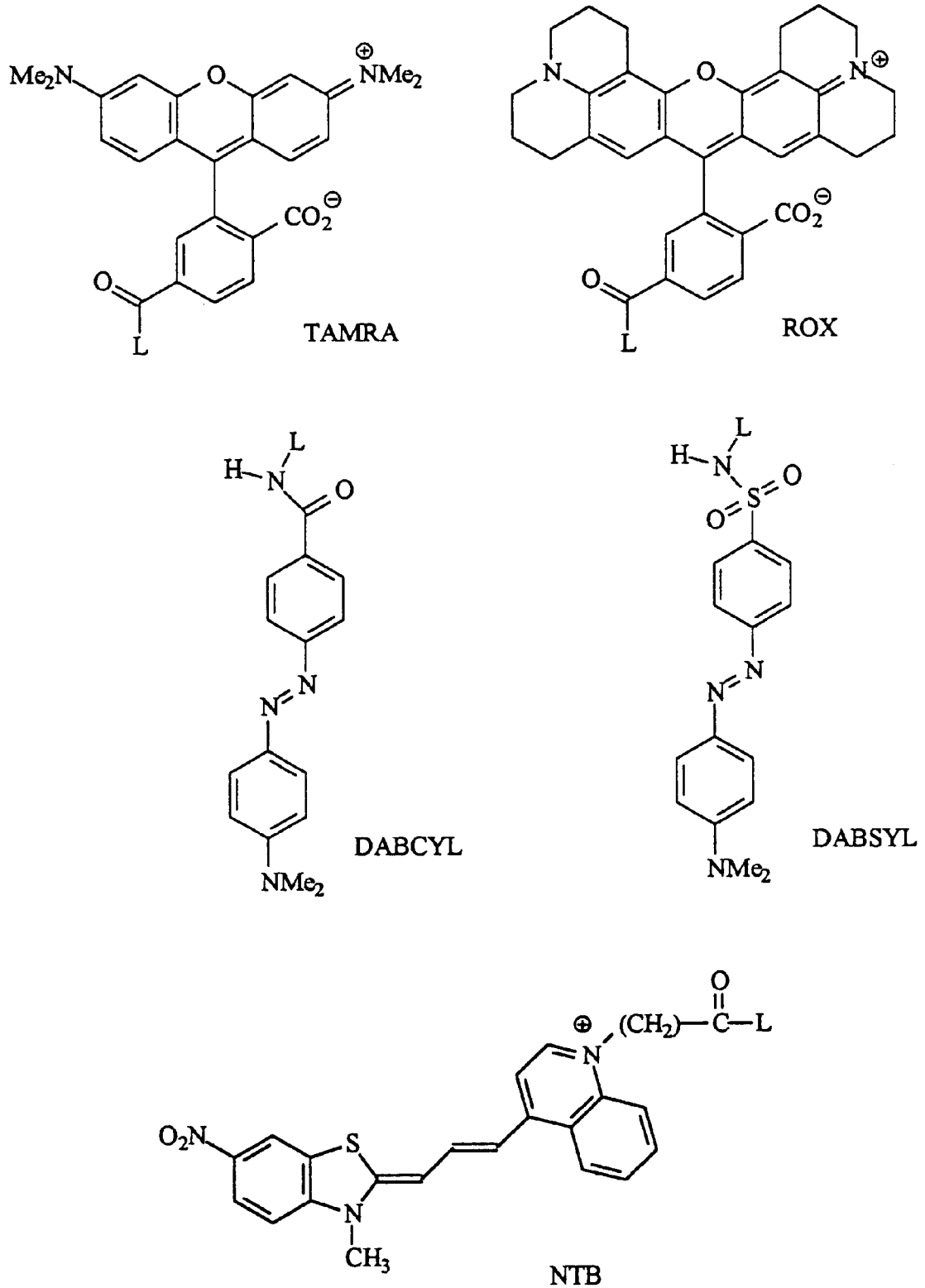

Another preferred class of labels include quencher moieties. Particularly preferred quenchers included but, are not limited to (i) rhodamine dyes selected from the group consisting of tetramethyl-6-carboxyrhodamine (TANRA), tetrapropano-6-carboxyrhodamine (ROX), and (ii) DABSYL, DABCYL, cyanine dyes including nitrothiazole blue (NTB), anthraquinone, malachite green, nitrothiazole, and nitroimidazole compounds and the like (FIG. 10).

Fluorescein (left) and rhodamine (right) derivatives of the present invention may bear the general structure and numbering system below, where L is a linker, and may be substituted at one or more of the numbered positions.

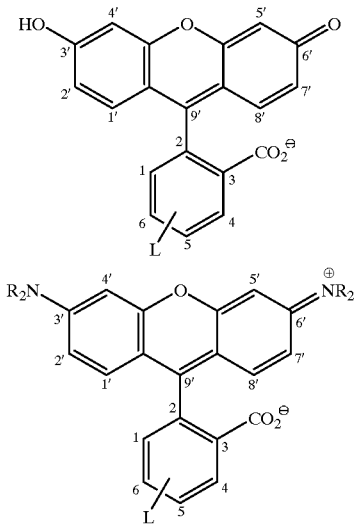

III. Methods Using Binary Probe and Clamp Compositions

Figure 2:
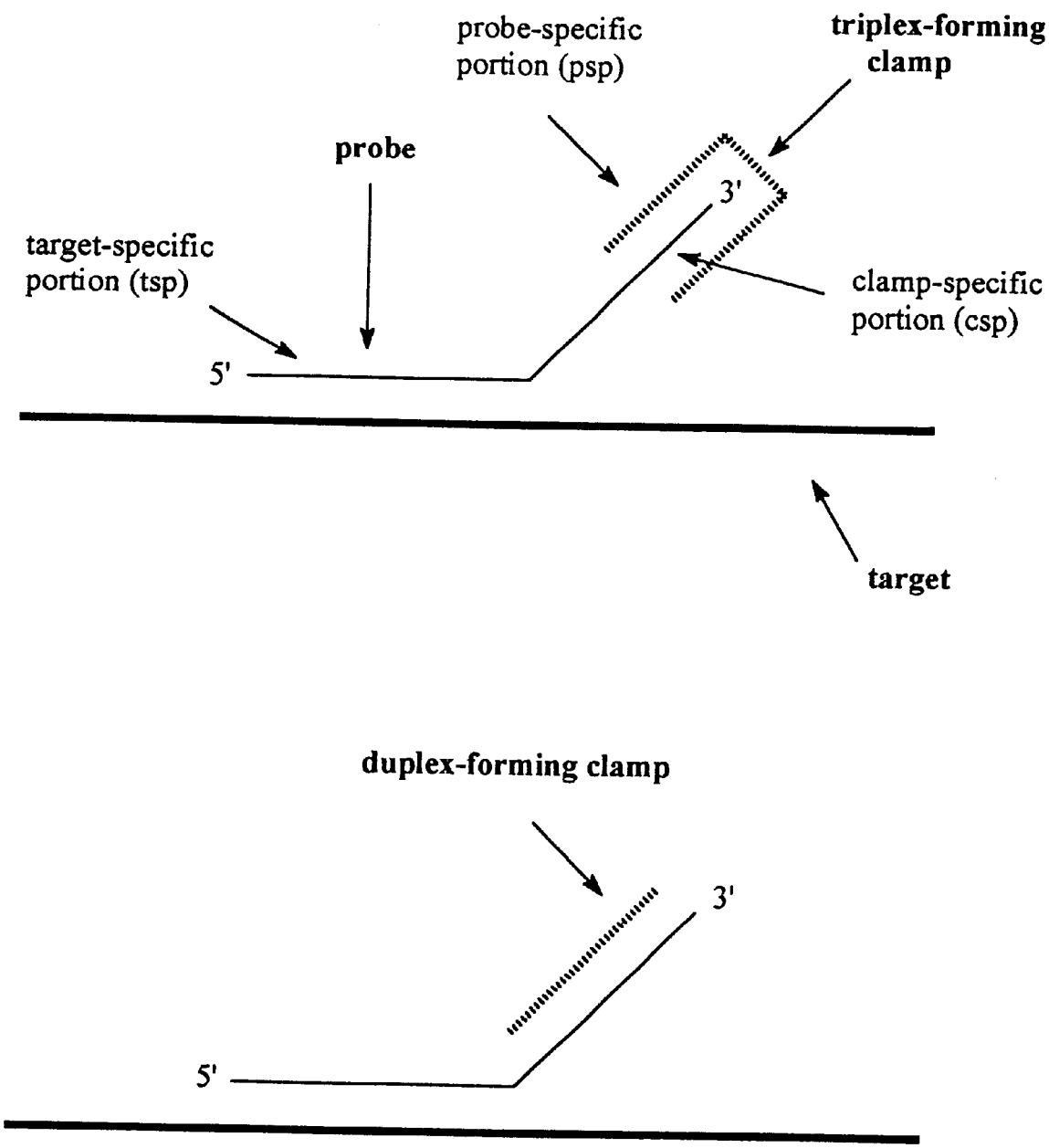

Binary probe and clamp compositions of the present invention may be used in any hybridization assay in which the probe hybridizes to complementary target (FIG. 2).

Figure 4:
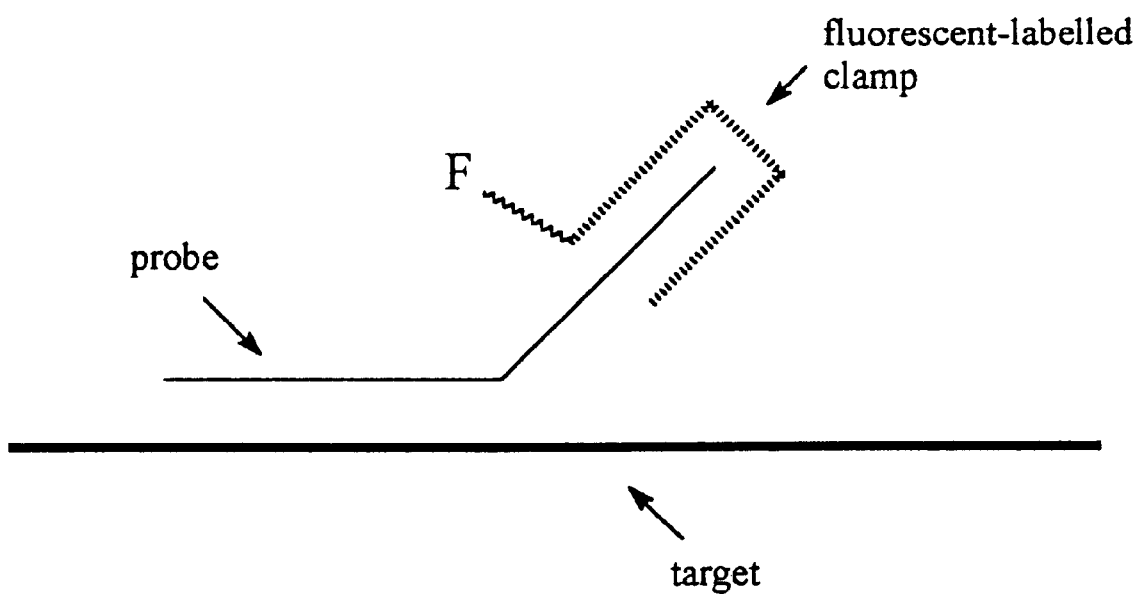

Hybridization without amplification can be detected and measured by fluorescence from a binary unlabelled probe and fluorescent-labelled clamp composition (FIG. 4). The method entails: i) hybridizing binary probe and clamp compositions to target, ii) washing or removing unbound composition, and iii) detecting and measuring fluorescence from the bound composition/target duplex.

In certain preferred embodiments, the binary probe and clamp composition may be labelled such that a single clamp sequence may be selected for hybridizing to many different probe sequences for economy, convenience, and facilitated dispensing and handling. A single clamp-specific portion may be incorporated into many probes which comprise different target-specific portions. A single, complementary clamp sequence, may then serve in many nucleic acid hybridization assays. For example, a labelled clamp prepared at the 2 μmole scale can provide >100,000 assays where approximately 10 pmole is required per assay. Unlabelled probes have cost and simplicity advantages when used in compositions with labelled clamps. Since labelling probes is expensive and laborious, this versatile utility of the binary probe and clamp composition is a highly desirable feature. Additionally, multiple loci of a target sample in a single reaction vessel can be assayed by probing with multiple compositions where each sequence is labelled with a different and spectrally resolvable fluorescent dye. The respective emission spectra from the fluorescent dye moieties within a reaction vessel must be sufficiently non-overlapping so that separate emission contributions can be resolved. The separate peaks may be quantitated, correlating to the relative amounts of target sequences, i.e. amplification products.

In a particularly preferred embodiment, the probes and clamps of the invention may be used in quantitative methods and reagents that, e.g. provide real time measurements of amplification products during PCR (Holland, 1991; Higuchi, 1992; Higuchi, 1993; Gelfand, 1993; Livak, 1996). The exonuclease assay (Taqman®) employing fluorescent dye-quencher probes (Livak, 1995) gives direct detection of polymerase chain reaction (PCR) products in a closed-tube system, with no sample processing beyond that required to perform the PCR. In the Taqman assay, the polymerase that conducts primer extension and amplifies the polynucleotide also displaces and cleaves a probe annealed to target by 5' to 3' exonuclease activity. In a Taqman-type assay, the probe is self-quenching, containing fluorescent dye and quencher moieties. Spectral overlap allows for efficient energy transfer (FRET) when the probe is intact (Clegg, 1992). When hybridized to target, the probe is cleaved during PCR to release a fluorescent signal that is proportional to the amount of target-probe hybrid present (Livak, 1996; Livak, 1998).

Figure 3:
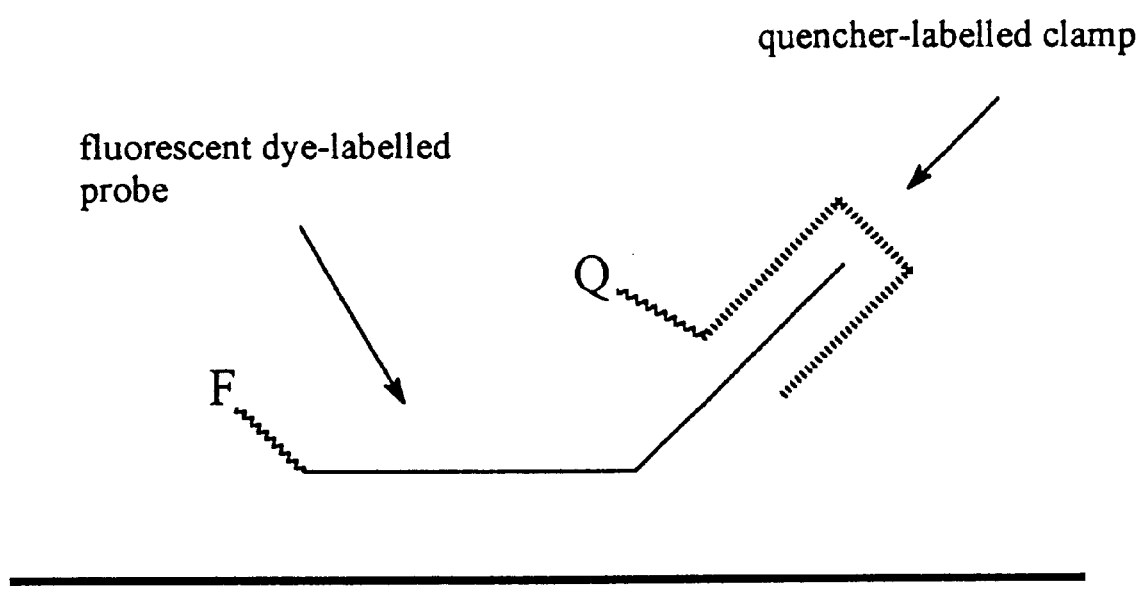
Figure 8:
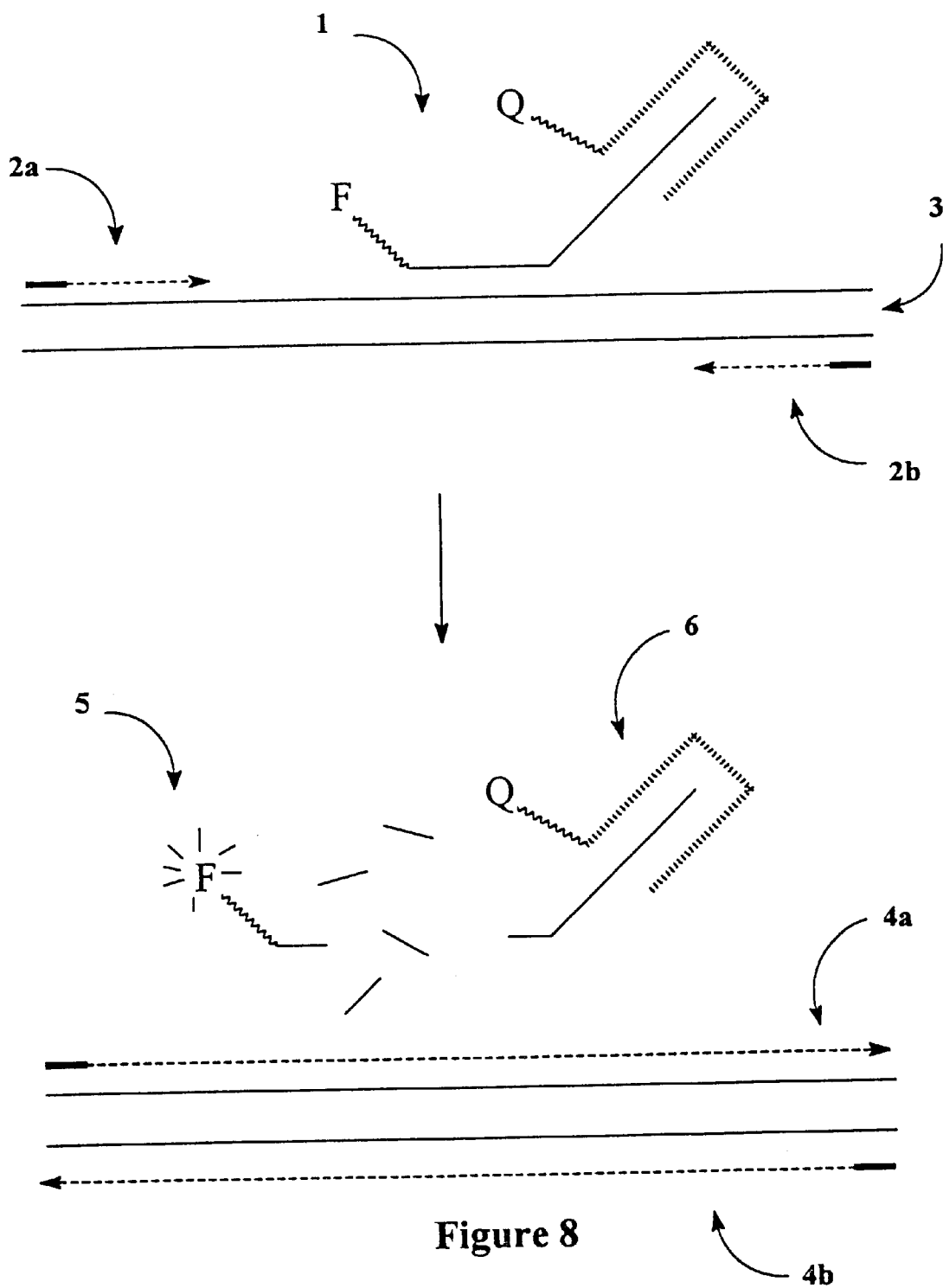

In a Taqman-type assay, polymerase with suitable exonuclease-activity can substantially cleave the probe of the binary composition during amplification to separate the fluorescent dye from the quencher dye. In a self-quenching binary probe and clamp composition of the present invention, when the probe is hybridized to the clamp, the proximity of the fluorescent dye to the quencher causes the fluorescence of the fluorescent dye to be quenched (FIG. 3). When the probe is not hybridized to the clamp, the fluorescence of the fluorescent dye is not quenched (FIG. 1). The clamp-specific portion of the probe remains bound to the probe-specific portion of the clamp after cleavage (FIG. 8).

A fluorescent dye-quencher pair for a particular binary probe and clamp composition is selected such that the emission spectrum of the fluorescent dye overlaps is with the absorption of the quencher. The probe may be labelled with either the fluorescent dye or the quencher and the clamp will then be labelled with the other. The quencher is released from its close proximity to the fluorescent dye upon cleavage so that the signal from the fluorescent dye is no longer quenched. An increase in fluorescence occurs which correlates directly and proportionally with the increase in copies of the PCR product (FIG. 8). By using real-time or end-point analysis, detection and quantitation of PCR products can be obtained by measuring the increase in fluorescence of cleaved, self-quenching fluorescent probes. Two or more self-quenching binary compositions consisting of probes with different dyes may be hybridized concurrently or sequentially to different sites on a target polynucleotide.

In this manner, hybridization events can be detected and measured by fluorescence. The hybridization event may be reversible, affected by conditions that typically melt or disrupt base-pairing, e.g. denaturants or heating. The presence or absence of specific target sequences can be detected in a sample.

Figure 5:
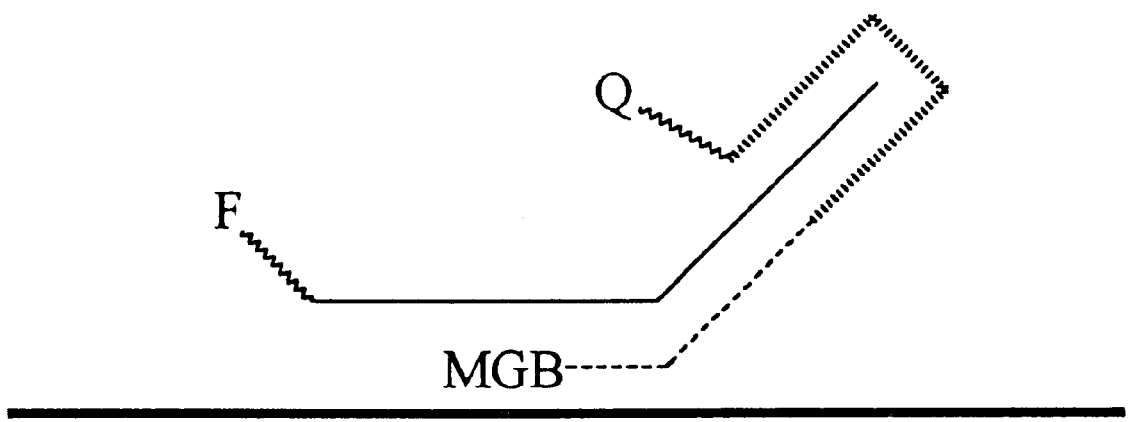

Self-quenching binary compositions may be further labelled, for example with hybridization-stabilizing moieties such as minor-groove binders (FIG. 5). The minor-groove binder may increase specificity and affinity of binding between the target and the probe.

Clearly, these methods may be generalized to include a plurality of independently detectable labels, e.g. fluorescent dyes having spectrally-resolvable emission spectra, e.g. to monitor the simultaneous detection and amplification of several target nucleic acids in a single reaction, so that a plurality of detection signals are monitored. Such multi-label systems are advantageous in applications requiring analysis of multiple probe experiments and multiple amplifications occurring in a single vessel. In such systems when the labels are fluorescent dyes, each dye can be identified by spectral resolution, thus enabling multiple target identification (Livak, 1996; Menchen, 1993; Bergot, 1994).

Binary probe and clamp compositions with self-quenching fluorescent dye-quencher moieties may be used in conjunction with a variety of nucleic acid amplification methods. Exemplary amplification schemes that may be employed with the system of the invention include PCR, ligase-based amplification schemes, such as ligase chain reaction (Barany, 1991), Q-beta replicase, and strand displacement amplification schemes (Walker, 1992).

Figure 7:
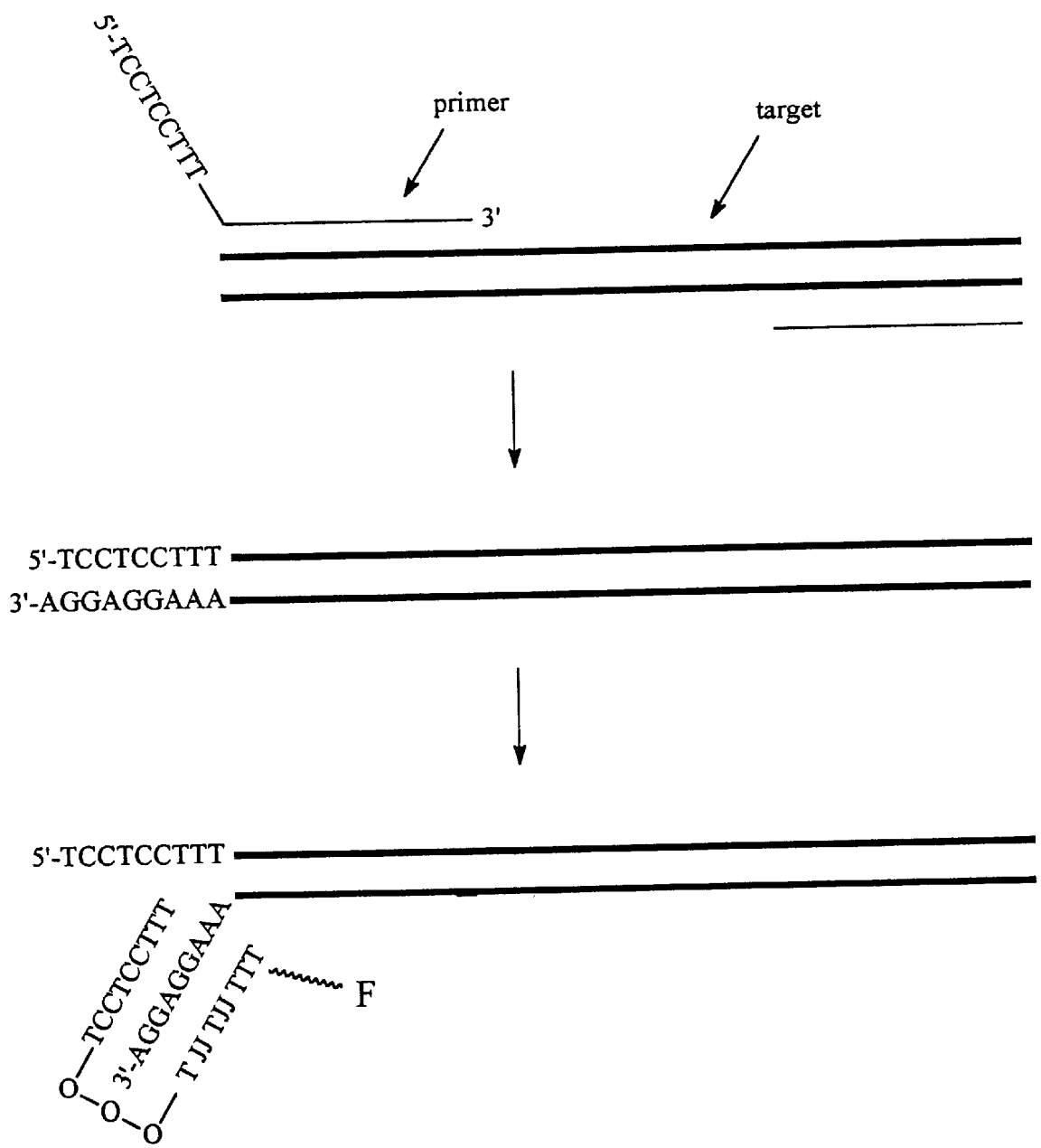

Binary primer and labelled clamp compositions can be used to amplify target sequences by PCR to generate labelled PCR products (FIGS. 6 and 7). The label of the resulting PCR products may be bound by hybridization with the clamp-specific portion of the primer. By these methods, unlabelled primers may be used, which are significantly less costly and labor- intensive to prepare than labelled primers, such as 5' fluorescent dye-labelled primers. Each unlabelled primer may have a conserved clamp-specific sequence, such as AAAGGAGGA-3' at the 5' terminus for binding to a conserved sequence clamp, containing the primer-specific sequence TCCTCCTTTT, and analogs therof Alternatively, the unlabelled primer may have a conserved homopyrimidine sequence at the 5' end which becomes part of the PCR product upon amplification. The labelled clamp has the same homopyrimidine sequence, to specifically form a detectable duplex or triplex structure with the homopurine complement sequence at a 3' terminus of the PCR product (FIG. 7). Thus, a single synthesis of a labelled clamp may suffice for many labelled-PCR experiments.

IV. EXAMPLES

The invention will be further clarified by a consideration of the following examples, which are intended to be purely exemplary of the present invention and not to in any way limit its scope.

Example 1

Synthesis of Labelled Probes

A. 5' fluorescent dye-probes

BAK: FAM-CTGCCCAGCCCCAGCCCAAAGGAGGA (SEQ. ID NO. 1)

GTT1: FAM-CCTGCAGGCCCGTGCCCGTAAAGGAGGA (SEQ. ID NO. 2)

NED-TGCTGGCACCAGACTTGCCCTCAAAGGAGGA (SEQ. ID NO. 3)

BAK—Bak polymorphism in the gene for human platelet membrane glycoprotein IIb (Lyman, 1990).

GTT1—human gene for glutathione S-transferase, theta-class (Pemble, 1994).

B. 3' quencher-probes

AAAGGAGGATGCTGGCACCAGACTTGCCCTC-NTB (SEQ. ID NO. 4)

AAAGGAGGATGCTGGCACCAGACTTGCCCTC-TAMRA (SEQ. ID NO. 5)

AAAGGAGGACCTGCAGGCCCGTGCCCGT-ROX (SEQ. ID NO. 6)

C. 5' quencher-2'-O-methyl RNA/DNA chimera probes

NTB-TGCTGGCACCAGACTTGCCCTCAAAGGAGGA (SEQ.ID NO.7)

TAMRA-TGCTGGCACCAGACTTGCCCTCAAAGGAGGA (SEQ. ID NO.8)

ROX-CCTGCAGGCCCGTGCCCGTAAAGGAGGA (SEQ. ID NO.9)

bold letters are 2'-O-methyl nucleotides

D. 3' fluorescent dye, 5-propynyl containing probes

AAAGGAGGATGCTGGCACCAGACTTGCCCTC-FAM (SEQ. ID NO. 10)

AAAGGAGGATGCTGGCACCAGACTTGCCCTC-VIC(SEQ. ID NO. 11)

AAAGGAGGACCTGCAGGCCCGTGCCCGT-TET (SEQ. ID NO. 12)

C and T(bold, underlined) are 5-propynyl cytidine and 5-propynyl thymine nucleotides respectively E. 2,6-diaminopurine (DAP) containing probes

AAAGGAGGATGCTGGCACCAGACTTGCCCTC-NTB (SEQ. ID NO. 13)

JOE-TGCTGGCACCAGACTTGCCCTCAAAGGAGGA (SEQ. ID NO. 14)

FAM-CCTGCAGGCCCGTGCCCGTAAAGGAGGA-(SEQ. ID NO. 15)

A (bold, underlined A) are DAP nucleotides (Kutyavin, Rhinehart, 1996)

F. 2-thiopyrimidine containing probes

NTB-TGCTGGCACCAGACTTGCCCTCAAAGGAGGA (SEQ. ID NO. 16)

JOE-TGCTGGCACCAGACTTGCCCTCAAAGGAGGA (SEQ. ID NO. 17)

AAAGGAGGACCTGCAGGCCCGTGCCCGT-FAM (SEQ. ID NO. 18)

T (bold, italicized T) are 2-thiopyrimidine nucleotides (Kutyavin, Rhinehart, 1996)

T

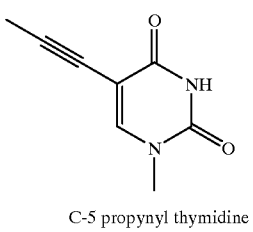

C-5 propynyl thymidine

C

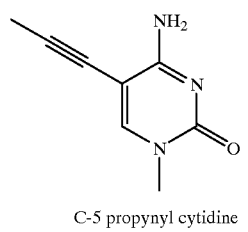

C-5 propynyl cytidine

A

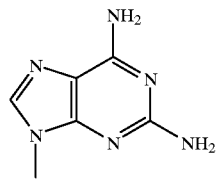

2,6-DAP

T

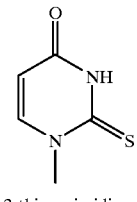

2-thiopyrimidine

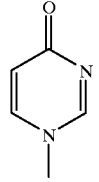

4(3H)-pyrimidone

Probes were synthesized at the 0.2 μmole scale on the Model 394 DNA/RNA synthesizer. The 5' fluorescent dyes were attached as fluorescent dye phosphoramidites (0.1M in acetonitrile) with an extended 120 second coupling time. The 5' fluorescent dye-labelled oligonucleotides were deprotected in concentrated ammonium hydroxide for 2 hours at 65 °C. The 3' quencher probes were synthesized with quencher supports having the structure below, and other structural variants (Mullah, 1997; Mullah, 1998). The label is attached to a linker which has attachment sites for the solid support S and the DMT-protected hydroxyl site for initiation of oligonucleotide synthesis. The solid support may be controlled-pore glass or polystyrene. After synthesis is complete, the ester bond is cleaved, separating the 3' labelled-oligonucleotide from the solid support with the structure below.

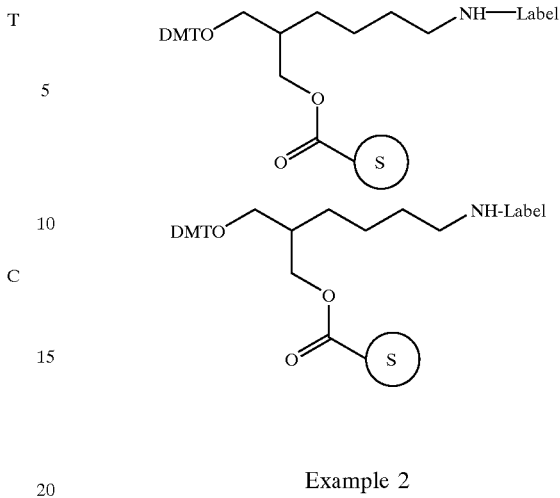

Example 2

Synthesis of PNA Clamps

Automated synthesis of PNA was performed using an ABI Model 394 DNA/RNA synthesizer or 433A peptide synthesizer (Perkin-Elmer Co.) according to the general procedures described in the synthesizer manufacturer's Users Manual, as well as Egholm, 1993.

PNA clamps were synthesized at 2–5 4 μmole scale essentially as previously reported (Dueholm, 1994). The carboxy-terminal lysine of PNA were prepared on a MBHA solid support, preloaded with t-Boc-lys(Fmoc). PNA with carboxy-terminal amides were synthesized either directly on an MBHA support or on a MBHA support pre-loaded with the t-Boc T PNA monomer. All resins were loaded to 0.1 to 0.25 mmole/g. Internal lysine residues (K) were coupled as t-Boc-lys(clbz) except in the preparation of clamp SEQ. ID NO. 23 which required internal labeling and was prepared with t-Boc-lys(Fmoc). A piperidine wash was typically performed following the capping step but was excluded when t-Boc-lys(Fmoc) was incorporated into the PNA assembly. A portion of a representative PNA structure is shown (FIG. 12) with thymine T, cytidine C, and pseudo-isocytidine J nucleobases. The spacer O, 2-[2-(2-aminoethoxy]acetic acid, is coupled as the Fmoc-amino protected synthon. One or more spacer O units act as a flexible, non-base pairing, hinge region in triple helix forming clamps (FIG. 13). Synthesis of PNA can be conducted on a MBHA (methylbenzhydrylamine) linker, high-loaded polystyrene support at 2–50 μmole scale by a cycle of steps. The cycle is conducted for each Boc-PNA monomer addition (Koch, 1997; Dueholm, 1994) and is summarized in the Table below.

TABLE

| PNA synthesis cycle on the Model 433A synthesizer | | | |
|---|---|---|---|
| Step | Function | Reagents delivered | Time |
| 1 | BOC removal | TFA/m-cresol, 95/5 | 6 min |
| 2 | Wash | DMF/DCM, 1/1 | 2 min |
| 3 | Wash | Pyridine/DMF, 5/95 | 2 min |
| 4 | Coupling | 5 equiv. BOC-PNA monomer (0.05 m), 4.5 equiv. HATU, DIEA | 15 min |
| 5 | Wash | DMF/DCM, 1/1 | 2 min |
| 6 | Capping | Acetic anhydride/DMF, 5/95 | 5 min |
| 7 | Wash | DMF/DCM, 1/1 | 2 min |

TABLE-continued

PNA synthesis cycle on the Model 433A synthesizer

| Step | Function | Reagents delivered | Time |
|---|---|---|---|
| 8 | Wash | Piperidine/DMF, 1/1 | 2 min |
| 9 | Wash | DMF/DCM, 1/1 | 2 min |

DIEA diisopropylethylamine
TFA trifluoroacetic acid
HATU 1-hydroxy-7-azabenzotriazole-tetramethyluronium hexafluorophosphate
DCM dichloromethane
DMF dimethylformamide The synthesis of PNA was performed with standard synthesis techniques and nucleobase ($A^{bz}$, $C^{bz}$, $G^{ibu}$, T) and primary amino (MMT, Fmoc or Boc) protecting groups. A 3 ml reaction vessel is used at the 5 μmole scale with a total reaction volume of 440 μl. At the end of synthesis, the PNA is cleaved with TFMSA (trifluoromethanesulfonic acid) at room temperature for 1 hour, followed by ether precipitation of the crude PNA.

Example 3

Synthesis of PNA/DNA Chimera Clamps

Automated synthesis of PNA/DNA chimera was performed using an Applied Biosystems Model 394 DNA/RNA synthesizer or 433A peptide synthesizer according to the general procedures described in the Users Manual as well as Uhlmann, 1996; Van der Vinayak, 1997.

The support used for PNA/DNA chimera synthesis is a non-swelling, high-cross linked polystyrene bead with a hydroxymethylbenzoic acid linker (Vinayak, 1997). PNA monomers for chimera synthesis use the monomethoxytrityl (MMT) group for primary amino protection. In the first step, the monomer, HATU and DIPEA, each dissolved in DMF/acetonitrile, 1/1, are delivered concurrently to the reaction cartridge. After 16 min, capping reagents are delivered. To minimize the tendency of the primary amino function of PNA to migrate or cyclize, the amino terminus is acetylated after removal of the final MMT group. Reagents have been described to link DNA and PNA moieties, and other procedures for chimera synthesis, cleavage, deprotection, and purification (Van der laan, 1997). In this approach, the chimera can be made continuously, in a single cartridge and on a single synthesizer.

Example 4
Labelling of Clamps
A. Quencher-PNA Clamp
NTB-O-TTTJJTJJT-OOO-TCCTCCTTT-OK (SEQ. ID NO. 19)
NTB-O-TTTJJTJJT-OOO-TCCTCCTTT-OKOKOK (SEQ. ID NO. 20)
NTB-O-TTTJJTJJT-OOO-TCCTCCTTT-OK-NTB (SEQ. ID NO. 21)
TAMRA-O-TCCTCCTTT-OOO-TTTJJTJJT (SEQ. ID NO. 22)
H-TCCTCCTTT-OK(TAMRA)O-TTTJJTJJT (SEQ. ID NO. 23)
NTB-TCCTCC-OOO-TTTJJTJJT (SEQ. ID NO. 24)
NTB-O-TCCTCCTT-OOO-TTJJTJJT (SEQ. ID NO. 25)
TAMRA-O-TCCTCCT-OOO-TJJTJJT (SEQ. ID NO. 26)
TAMRA-O-TCCTCCTT (SEQ. ID NO. 27)

B. Fluorescent Dye-PNA Clamp
FAM-O-TCCTCCTTT-OOO-TTTJJTJJT (SEQ. ID NO. 28)
VIC-O-TCCTCCTTT-OOO-TTTJJTJJT (SEQ. ID NO. 29)
TET-O-TCCTCCTT (SEQ. ID NO. 30)
C. MGB, Label-PNA Clamp
NTB-O-TTTJJTJJT-OOO-TCCTCCTTT-OK-MGB1 (SEQ. ID NO. 31)
TAMRA-O-TTTJJTJJT-OOO-TCCTCCTTT-OK-MGB1 (SEQ. ID NO. 32)
H-O-TTTJJTJJT-OOO-TCCTCCTTT-OK-CDPI$_3$ (SEQ. ID NO. 33)
NTB-O-TTTJJTJJT-OOO-TCCTCCTTT-OK-CDPI$_3$ (SEQ. ID NO. 34)
D. Quencher and Minor Groove Binder Labelled 2'-O-methyl RNA Clamps
TAMRA-O-TCCTCCTTT-OOO-TTTJJTJJT (SEQ. ID NO. 35)
H-TCCTCCTTT-OK(TAMRA)O-TTTJJTJJT (SEQ. ID NO. 36)
NTB-TCCTCC-OOO-TTTJJTJJT (SEQ. ID NO. 37)
NTB-O-TCCTCCTT-OOO-TTJJTJJT (SEQ. ID NO. 38)
TAMRA-O-TCCTCCT-OOO-TJJTJJT (SEQ. ID NO. 39)
TAMRA-O-TCCTCCTT (SEQ. ID NO. 40)
E. 5-propynyl containing PNA clamp
NTB-O-T<u>CC</u>T<u>CC</u>TT-OOO-TTTJJTJJT (SEQ. ID NO. 41)
TAMRA-O-T<u>CC</u>T<u>CC</u>T-OOO-TJJTJJT (SEQ. ID NO. 42)
PNA sequences written with amino terminal at left, carboxyl terminal at right 2'-O-methyl RNA sequences are written 5' on left, 3' on right Clamp sequences SEQ. ID NOS. 19–21,22,23,28,29, 31–37 were designed to clamp the sequence: AAAGGAGGA-3' at the 3' end of the probe. Clamps SEQ. ID NOS. 25,27,38,40 and 24,26,30,39 bind the shorter sequences of AAGGAGGA and AGGAGGA respectively. Clamps SEQ. ID NOS. 22–26,28,29,35–39 contain a hinge region oriented toward the 5' end of the probe and terminii complementary to the 3' terminus of the probe, while clamps SEQ. ID NOS. 19–21,31–34 have a hinge region oriented at the 3' terminus of probe and terminii complementary toward the 5' end of the probe (FIG. 13). Clamps SEQ. ID NOS. 19 and 22 are representative of the most stable orientations of PNA to DNA. The PNA/DNA hybrid is in the antiparallel orientation when the amino terminus of PNA is paired with the 3' terminus of DNA, and the carboxyl terminus of PNA is paired with the 5' terminus of DNA. The amino end of the Watson-Crick base-pairing portion of the PNA clamps, (C)-TTTCCTCCT-(N), is in the anti-parallel orientation toward the 3' terminus of the probe. The carboxyl end of the Hoogsteen base-pairing portion of the PNA clamps, (N)-TTTJJTJJTC-(C) is in the parallel orientation toward the 3' terminus of the probe. These orientations have been shown to be most stable in (PNA)$_2$/DNA triplexes (Egholm, 1995, Egholm, 1993). Clamps SEQ. ID NOS. 27,30,40 form duplex structures with a probe, while clamps SEQ. ID NOS. 19–26,28,29,31–39,41,42 form triplex structures with a probe.

All labeling reactions for clamps as reported are for a 2 μmole synthesis preparation. Prior to internal and amine terminus labeling, the Fmoc protection group was removed from the lysine (K) side chain by treatment of the support-bound protected PNA with 4:1 DMF:piperidine for three hours at room temperature. The amine terminus t-Boc group was removed by treatment of the support bound PNA with 19:1 TFA:meta-cresol for 10 minutes. The support was thoroughly washed with DMF and DCM following the deprotection. Carboxy terminal and internal labels were attached to the lysine side chain. Carboxy terminal labeling was performed prior to amine terminus deprotection and labeling, except for clamp SEQ. ID NO. 21 where labeling of both terminii was performed simultaneously. PNA were labeled at the carboxy terminus with MGB1 and CDPI3, and NTB and TAMRA at the amine terminus.

TAMRA and NTB Labeling

Labeling was performed with 5 mg of NHS ester of TAMRA or NTB dissolved in 100 µl DMF or NMP and 10 µl DIEA added to the support bound PNA and allowed to react for 2 to 18 hours (typically overnight). The support was washed following the labeling with DMF and subsequently DCM prior to cleavage.

MGB1 Labeling

The carboxylic acid of MGB1 (Gong, 1997) (5 mg, 0.010 mmole) was dissolved in 100 µl DMF (FIG. 11) and activated by the addition of 0.95 equivalents HATU (0.2 m in DMF) and 5 µl DIEA. The activated MGB1 solution was added to the support-bound PNA and allowed to couple for 1 hour at room temperature. The resin was then washed with DMF and DCM, followed by cleavage.

CDPI Labeling

CDPI$_3$ (FIG. 11) was attached to the PNA by three consecutive couplings of Fmoc-CDPI (Lukhtanov, 1995) to give CDPI$_3$-labelled PNA. The CDPI monomer unit, 1,2-dihydro-(3H)-pyrrolo[3,2-e]indole-7-carboxylate, protected with Fmoc (5 mg, 0.012 mmole) was dissolved in 100 µl NMP and activated by 0.95 equivalents HATU (0.2M in DMF) and 2 equivalents DIEA (0.4 m in DMF). After one hour at room temperature, the activated Fmoc-CDPI solution was added to the support bound PNA and allowed to couple for another hour at room temperature. The resin was washed following the coupling with 20 ml DMF. The Fmoc was removed by treatment of the resin support with 1:4 piperidine:DMF for 10 minutes at room temperature. This coupling and deprotection cycle was repeated two additional times for a total of 3 manual couplings.

Example 5

Rate of Hybridization of Probe and Clamp

The rate of hybridization of three clamps (SEQ. ID NOS. 19, 20, 21) to a probe (SEQ. ID NO. 1) was measured as a function of quenching. The decrease in fluorescence intensity [F] from FAM dye of the probe upon hybridization and quenching by the clamp quencher NTB was measured at 60° C. on the ABI Model 7700. Equimolar amounts of the clamp (100 nM) and the probe (100 nM) were mixed at 95° C. for I minute, cooled to 60° C. and [F] was measured for 29 minutes (FIG. 14). A significant acceleration of quenching of the probe was achieved with a four-fold excess of clamp (400 nM) where quenching was virtually complete with each of the three clamps within 15 seconds (FIG. 15).

Example 6

Exonuclease/amplification Assay with Binary Probe and Clamp Compositions

The following reagents were mixed and 25 µl dispensed into each sample vessel for PCR:

12.5 µl Universal PCR Master Mix (PE Biosystems, P/N 4304437) containing Tris-HCl, glycerol, 10 mm MgCl$_2$, dATP, dCTP, deaza dGTP, dUTP, 0.1 µ/µl of Amplitaq Gold DNA polymerase, Amperase UNG, and passive reference 900 nM (final concentration): GTT1 forward target primer:
5' GCAAATATAAGGTCCCTGACTACTGGTA 3' (SEQ. ID NO. 44)

900 nM (final concentration): GTT1 reverse target primer:
5'GTGCTGCCATGCCAGGTACT 3' (SEQ. ID NO. 45)

100 nM probe and 400 nM clamp composition

10 µl (approximately 20 ng) genomic target DNA

Target samples were amplified by thermal cycling conditions that begin with 2 min at 50° C., 10 min hold at 95° C. and then 40 cycles of 15 sec denaturation at 95° C. and 1 annealing and extension at 60° C. Thermal cycling and real-time fluorescence detection may be conducted on an ABI PRISM™ 7700 sequence detection system (Perkin-Elmer Co.). A preferred end-point detection system is the ABI PRISM 7200 Sequence Detection System.

The results of an exonuclease assay can be analyzed using two parameters; the Rn value and the $C_t$ value. The Rn value is the increase in fluorescence during PCR, or more exactly, the ratio of the fluorescence of a fluorescent dye and the fluorescence of a passive fluorescent reference dye at the end of a PCR experiment, i.e. Rn (target)=Emission intensity of target probe÷Emission intensity of passive reference. The $C_t$ value, or threshold cycle number, is the PCR cycle number at which the fluorescence ratio is distinguishable from the background. For a given fluorescent dye and a fixed concentration of target, both the Rn and $C_t$ values reflect the efficiency of the quencher. The term, ΔRn is the increase in fluorescence during PCR with subtraction of background or initial fluorescence.

The products of PCR were measured with real-time detection of cleavage of binary probe and clamp compositions. The BAK target was sequentially amplified in the presence of binary probe and clamp compositions: 400 nM clamp (SEQ. ID NOS. 19, 20, 21), 100 nM probe (SEQ. ID NO. 1) on the ABI Model 7700 (FIG. 16). The change in fluorescence, ΔRn, was plotted versus amplification cycles. The cycle at which the change in fluorescence is distinguishable from background, $C_T$, indicates the presence of target sequence. When background fluorescence is not subtracted, Rn, the difference in quenching efficiency of the three clamps is pronounced (FIG. 17). Clamp SEQ. ID NO. 21 with two NTB labels quenches better than clamp SEQ. ID NO. 19. Clamp SEQ. ID NO. 20 with three lysine labels quenches better than clamp SEQ. ID NO. 19 with one lysine.

The GTT1 target was sequentially amplified in the presence of: 1) binary probe and clamp compositions: 100 nM probe (SEQ. ID NO. 2) and 400 nM clamp (SEQ. ID NOS. 20, 21), and 2) Taqman probe bearing a fluorescent dye and a quencher:

5' FAM-CCTGCAGGCCCGTGCCCGT-TAMRA 3' SEQ. ID NO. 43

Real-time PCR detection was measured on the ABI Model 7700 with subtraction of background fluorescence, ΔRn (FIG. 18), and without subtraction of background fluorescence Rn (FIG. 19). No significant difference in CT was measured when comparing the binary probe/clamp compositions and the Taqman probe.

All publications and patent applications are herein incorporated by reference to the same extent as if each individual publication or patent application was specifically and individually indicated to be incorporated by reference.

Although only a few embodiments have been described in detail above, those having ordinary skill in the molecular biology and chemistry arts will clearly understand that many modifications are possible in the preferred embodiment without departing from the teachings thereof. All such modifications are intended to be encompassed within the following claims.

We claim:

1. A binary composition for hybridizing to a target polynucleotide sequence comprising:

a probe comprising a target-specific portion and a clamp-specific portion wherein the target-specific portion is capable of sequence-specific binding to a target polynucleotide sequence; and a clamp comprising two probe-specific portions, one or more labels and at least one nucleic acid analog selected from a nucleobase analog, a sugar analog, and an internucleotide analog;

wherein the probe is hybridized to the clamp by sequence-specific binding of the probe-specific portion of the clamp to the clamp-specific portion of the probe, and the clamp is incapable of sequence-specific binding to the target polynucleotide; and wherein the two probe-specific portions are capable of sequence-specific binding to the clamp-specific portion of the probe to form a triplex.

2. The binary composition of claim 1 wherein the probe comprises 6 to 100 nucleotides.

3. The binary composition of claim 1 wherein the clamp-specific portion of the probe comprises purine nucleotides.

4. The binary composition of claim 1 wherein the probe-specific portion of the clamp comprises pyrimidine nucleobase analogs.

5. The binary composition of claim 1 wherein the clamp comprises 6 to 50 nucleic acid analogs.

6. The binary composition of claim 1 wherein the clamp sequence comprises $(CAG)_n$ where n=1–10.

7. The binary composition of claim 1 wherein the clamp sequences include $(TCC)_n$ and nucleic acid analogs which bind the probe sequence $(GGA)_n$ where n=1–10.

8. The binary composition of claim 1 wherein the probe comprises a nucleic acid analog selected from the group consisting of a nucleobase analog, a sugar analog, and an internucleotide analog.

9. The binary composition of claim 8 wherein the nucleobase analog is selected from the group consisting of C-5- alkyl pyrimidine, 2,6-diaminopurine, 2-thiopyrimidine, C-5-propyne pyrimidine, 7-deazapurine, isocytidine, pseudo-isocytidine, isoguanosine, 4(3H)-pyrimidone, hypoxanthine, 8-oxopurine, and universal base.

10. The binary composition of claim 8 wherein the sugar analog is selected from the group consisting of 2'-O-alkyl-ribonucleotides, 2'-O-methyl-ribonucleotides, 2'-O-allyl-ribonucleotides, 2'-allyl ribonucleotides, 2'-halo-ribonucleotides, 2'-O-methoxyethyl-ribonucleotides, 2'-branching group-ribonucleotides, 2'-O-branching group-ribonucleotides, 4'-α-anomeric nucleotides, and 1'-α-anomeric nucleotides.

11. The binary composition of claim 8 wherein the internucleotide analog is selected from the group consisting of 2-aminoethylglycine (PNA), 2'-5'-linkage, inverted 3'-3' linkage, inverted 5'-5' linkage, phosphorothioate, methyl phosphonate, non-bridging N-substituted phosphoramidate, alkylated phosphotriester branched structure, and 3'-N-phosphoramidate.

12. The binary composition of claim 1 wherein the clamp comprises a non base-pairing, non-nucleosidic linker.

13. The binary composition of claim 1 wherein the clamp comprises one or more 2-aminoethylglycine (PNA) monomer units.

14. The binary composition of claim 1 wherein the clamp has one or more labels wherein the labels are attached at sites on the clamp selected from a terminus, a nucleobase, an internucleotide linkage, a sugar, an amino group, a sulfide group, and a carboxyl group.

15. The binary composition of claim 1 wherein the probe comprises a one or more labels.

16. The binary composition of claim 15 wherein the one or more labels are attached at sites each selected from a 5' terminus, a 3' terminus, a nucleobase, an internucleotide linkage, and a sugar.

17. The binary composition of claim 1 or 15 wherein the one or more labels are each selected from hybridization-stabilizing moieties, fluorescent dyes, fluorescence quenchers, chemiluminescent dyes, amino acids, and affinity ligands.

18. The binary composition of claim 17 wherein the chemiluminescent dyes are selected from the group consisting of chemiluminescent precursors having the structure

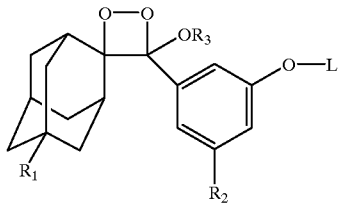

where $R_1$ is hydrogen or halogen; $R_2$ is phosphate, galactoside, glucoside, glucuronide, trialkylsilyloxy, acyloxy, or hydrogen; $R_3$ is methyl, ethyl, lower alkyl; and L is a linker.

19. The binary composition of claim 17 wherein the hybridization-stabilizing moieties are selected from the group consisting of minor groove binders, intercalators, and cross-linking functional groups.

20. The binary composition of claim 19 wherein the minor groove binders are selected from the group consisting of Hoechst 33258, $CDPI_{1-3}$, MGB1, netropsin, and distamycin.

21. The binary composition of claim 17 wherein the fluorescent dyes are selected from the group consisting of FAM, TET, HEX, JOE, TAMRA, ROX, VIC, NED, 4,7-dichloro-fluorescein, 4,7-dichloro-rhodamine, and cyanines.

22. The binary composition of claim 17 wherein the fluorescence quenchers are selected from the group consisting of TAMA, NTB, ROX, DABCYL, DABSYL, malachite green, and cyanines.

23. The binary composition of claim 18 wherein the affinity ligands are selected from the group consisting of biotin, dinitrophenyl, digoxigenin, cholesterol, polyethyleneoxy, and peptides.

24. The binary composition of claim 1 wherein the probe-specific portion of the clamp includes sequences $(TCC)_n$ and $(TJJ)_n$ where n=1–10 and J is pseudo-isocytosine.

25. A method for detecting polymerase chain reaction products comprising:
providing a binary probe and clamp composition comprising:
a probe comprising a target-specific portion and a clamp-specific portion and one or more labels wherein the target-specific portion is capable of sequence-specific binding to a target polynucleotide sequence; and
a clamp comprising a probe-specific portion, one or more labels, and at least one nucleic acid analog selected from a nucleobase analog, a sugar analog, and an internucleotide analog;
wherein the probe is hybridized to the clamp by sequence-specific binding of the probe-specific portion of the clamp to the clamp-specific portion of the probe, and the clamp is incapable of sequence-specific binding to the target polynucleotide;
hybridizing the target-specific portion of the probe to the target polynucleotide sequence;
hybridizing the probe-specific portion of the clamp to the clamp-specific portion of the probe; and
amplifying, the target with a DNA polymerase having an exonuclease activity, PCR primers, and nucleoside 5' triphosphates,
cleaving the probe by exonuclease activity of the polymerase, and
detecting the labels whereby the polymerase chain reaction products are detected.

26. The method of claim 25 wherein the clamp-specific portion of the probe and the probe-specific base-pairing portion of the clamp form a triplex.

27. The method of claim 25 wherein the labels are detected by monitoring the emitted fluorescence in real-time or at the end-point of target amplification.

28. A method for labelling polymerase chain reaction products comprising:
providing a primer comprising a target-specific portion and a clamp-specific portion wherein the target-specific portion is capable of sequence-specific binding to a target polynucleotide sequence; and
a clamp comprising a primer-specific portion and one or more labels wherein the primer-specific portion is capable of sequence-specific binding to the clamp-specific portion of the primer; and
amplifying the target with a DNA polymerase, one or more binary primer and clamp compositions, one or more opposing strand primers, and nucleoside 5' triphosphates;
wherein one or more labelled polymerase chain reaction products result.

29. The method of claim 28 wherein the label is a detectable fluorescent dye.

30. A method for detecting polymerase chain reaction products comprising:

providing one or more primers comprising a target-specific portion at the 3' end and a homopyrimidine sequence portion at the 5' end wherein the target-specific portion is capable of sequence-specific binding to a target polynucleotide sequence; and a clamp comprising the same homopyrimidine sequence as contained in the one or more primers and one or more labels;

amplifying the target with a DNA polymerase, one or more opposing strand primers, and nucleoside 5' triphosphates; and detecting the labels, wherein the homopyrimidine sequence of the clamp binds to its homopurine complement at a 3' terminus of the polymerase chain reaction product, and whereby the polymerase chain reaction products are detected.

31. The method of claim 30 wherein the label is a detectable fluorescent dye.

32. A kit comprising:

a probe comprising one or more labels, a target-specific portion and a clamp-specific portion wherein the target-specific portion is capable of sequence-specific binding to a target polynucleotide sequence; and a clamp comprising a probe-specific portion, one or more labels, and a nucleic acid analog selected from the group consisting of a nucleobase analog, a sugar analog, and an internucleotide analog;

wherein the probe-specific portion is capable of sequence-specific binding to the clamp-specific portion of the probe and the clamp is incapable of sequence-specific binding to the target polynucleotide; and wherein the labels are selected from the group consisting of hybridization-stabilizing moieties, fluorescent dyes, fluorescence quenchers, chemiluminescent dyes, amino acids, and affinity ligands.

33. The kit of claim 32 wherein the probe-specific portion of the clamp comprises one or more 2-aminoethylglycine (PNA) monomer units.

34. The kit of claim 32 wherein the probe-specific portion of the clamp comprises. a non base-pairing, non-nucleoside linker.

35. The kit of claim 32 wherein the probe-specific portion of the clamp comprises nucleobase analogs selected from the group consisting of C-5-alkyl pyrimidine, 2,6-diaminopurine, 2-thiopyrimidine, C-5-propyne pyrimidine, 7-deazapurine, isocytidine, pseudo-isocytidine, isoguanosine, 4(3H)-pyrimidone, hypoxanthine, 8-oxopurine, and universal base.

36. The kit of claim 32 wherein the clamp-specific portion of the probe comprises nucleobase analogs selected from the group consisting of C-5-alkyl pyrimidine, 2,6-diaminopurine, 2-thiopyrimidine, C-5-propyne pyrimidine, 7-deazapurine, isocytidine, pseudo-isocytidine, isoguanosine, 4(3H)-pyrimidone, hypoxanthine, 8-oxopurine, and universal base.

37. The kit of claim 32 wherein the labels are selected from the group consisting of minor groove binders, intercalators, and cross-linking functional groups.

38. The kit of claim 32 wherein the probe label and the clamp label form a fluorescent dye-quencher pair.

39. A kit comprising:

more than one probe wherein each probe has a different target-specific portion sequence and a single clamp-specific portion sequence, wherein the target-specific portion sequences are capable of sequence-specific binding to target polynucleotide sequences; and a clamp comprising a probe-specific portion, one or more labels, and a nucleic acid analog selected from the group consisting of a nucleobase analog, a sugar analog, and an internucleotide analog;

wherein the probe-specific portion is capable of sequence-specific binding to the clamp-specific portion of the probe and the clamp is incapable of sequence-specific binding to the target polynucleotide wherein the labels are selected from the group consisting of hybridization-stabilizing moieties, fluorescent dyes, fluorescence quenchers, chemiluminescent dyes, amino acids, and affinity ligands.

* * * * *